US009750608B2

(12) United States Patent
Spence et al.

(10) Patent No.: US 9,750,608 B2
(45) Date of Patent: Sep. 5, 2017

(54) SYSTEMS AND METHODS FOR INTRODUCING ELEMENTS INTO TISSUE

(71) Applicant: Mitralign, Inc., Tewksbury, MA (US)

(72) Inventors: Paul A. Spence, Louisville, KY (US); Donald S. Baim, Westwood, MA (US); Edward I. McNamara, Chelmsford, MA (US); Hiroatsu Sugimoto, Cambridge, MA (US); Joseph P. Lane, Methuen, MA (US); Christopher Lee, Tewksbury, MA (US); Jason H. Robinson, Windham, NH (US); Aaron M. Call, Mesa, AZ (US); Richard J. Morrill, North Billerica, MA (US)

(73) Assignee: MITRALIGN, INC., Tewksbury, MA (US)

( * ) Notice: Subject to any disclaimer, the term of this patent is extended or adjusted under 35 U.S.C. 154(b) by 0 days.

(21) Appl. No.: 14/462,177

(22) Filed: Aug. 18, 2014

(65) Prior Publication Data

US 2015/0051697 A1 Feb. 19, 2015

Related U.S. Application Data

(62) Division of application No. 11/685,239, filed on Mar. 13, 2007, now Pat. No. 8,845,723.

(51) Int. Cl.
*A61F 2/24* (2006.01)
*A61B 17/00* (2006.01)
(Continued)

(52) U.S. Cl.
CPC ........ *A61F 2/2466* (2013.01); *A61B 17/0057* (2013.01); *A61B 17/00234* (2013.01);
(Continued)

(58) Field of Classification Search
CPC .......... A61B 17/00234; A61B 17/0487; A61B 19/54; A61B 2017/00637; A61B 17/0401;
(Continued)

(56) References Cited

U.S. PATENT DOCUMENTS 2,143,910 A   1/1939   Didusch
3,674,014 A   7/1972   Tillander
(Continued)

FOREIGN PATENT DOCUMENTS

EP          1016377       7/2000
WO     WO 9604852        2/1996
(Continued)

OTHER PUBLICATIONS

Cardiac Surgery Renaissance, Anatomical Landscape; Composite Profile of CABG and Valve Procedures, Apr. 25, 1996, Cardiology Roundtable Interviews.
(Continued)

*Primary Examiner* — Jing Ou
(74) *Attorney, Agent, or Firm* — Leason Ellis LLP

(57) ABSTRACT

A system is provided for delivering respective anchors into spaced apart locations along an annulus of a mitral valve. The system includes a first catheter member having a first lumen formed therein for receiving a first guide wire and also includes a second catheter member that is configured to move between an expanded position and a collapsed position relative to the first catheter member. The second catheter member has a lumen formed therein for receiving a second guide wire when the second catheter member is in the expanded position. The second catheter member is fixedly connected to the first catheter member by a first connector (that defines first and second living hinges) which
(Continued)

is configured to deploy under a select condition to automatically cause the second catheter member to move to the expanded position.

20 Claims, 25 Drawing Sheets

(51) Int. Cl.
*A61B 17/04* (2006.01)
*A61B 17/06* (2006.01)
*A61B 90/00* (2016.01)

(52) U.S. Cl.
CPC ...... *A61B 17/0401* (2013.01); *A61B 17/0469* (2013.01); *A61B 17/0487* (2013.01); *A61B 17/06166* (2013.01); *A61F 2/2427* (2013.01); *A61F 2/2442* (2013.01); *A61F 2/2445* (2013.01); *A61B 17/0467* (2013.01); *A61B 90/39* (2016.02); *A61B 2017/00243* (2013.01); *A61B 2017/00637* (2013.01); *A61B 2017/00659* (2013.01); *A61B 2017/048* (2013.01); *A61B 2017/0411* (2013.01); *A61B 2017/0417* (2013.01); *A61B 2017/0419* (2013.01); *A61B 2017/0464* (2013.01); *A61B 2017/0488* (2013.01); *A61B 2017/0496* (2013.01); *A61B 2017/0619* (2013.01); *A61B 2090/0811* (2016.02); *A61B 2090/3966* (2016.02)

(58) Field of Classification Search
CPC .... A61B 2017/0417; A61B 2017/0496; A61B 17/0057; A61B 17/0467; A61B 2017/00243; A61B 2017/00659; A61B 2017/0419; A61B 2017/0488; A61B 2019/4857; A61B 2017/048; A61B 17/06166; A61B 17/0469; A61B 2090/3966; A61B 2017/0411; A61B 2017/0464; A61B 2017/0619; A61B 90/39; A61B 2090/0811; A61F 2/2427; A61F 2/2466; A61F 2/2442; A61F 2/2445
See application file for complete search history.

(56) References Cited

U.S. PATENT DOCUMENTS

| | | | |
|---|---|---|---|
| 3,794,041 A | 2/1974 | Frei et al. | |
| 3,841,521 A | 10/1974 | Jarvik | |
| 3,959,960 A | 6/1976 | Santos | |
| 3,986,493 A | 10/1976 | Hendren, III | |
| 3,995,619 A | 12/1976 | Glatzer | |
| 4,042,979 A | 8/1977 | Angell | |
| 4,055,861 A | 11/1977 | Carpentier et al. | |
| 4,258,705 A | 3/1981 | Sorensen et al. | |
| 4,369,787 A | 1/1983 | Lasner et al. | |
| 4,489,446 A | 12/1984 | Reed | |
| 4,532,926 A | 8/1985 | O'Holia | |
| 4,809,713 A | 3/1989 | Grayzel | |
| 4,917,698 A | 4/1990 | Carpentier et al. | |
| 4,945,912 A | 8/1990 | Langberg | |
| 5,016,353 A | 5/1991 | Iten | |
| 5,041,129 A | 8/1991 | Hayhurst et al. | |
| 5,041,130 A | 8/1991 | Cosgrove et al. | |
| 5,061,277 A | 10/1991 | Carpentier et al. | |
| 5,104,407 A | 4/1992 | Lam et al. | |
| 5,123,914 A | 6/1992 | Cope | |
| 5,171,232 A | 12/1992 | Castillo et al. | |
| 5,192,302 A | 3/1993 | Kensey et al. | |
| 5,201,880 A | 4/1993 | Wright et al. | |
| 5,203,777 A | 4/1993 | Lee | |
| 5,304,190 A | 4/1994 | Reckelhoff et al. | |
| 5,306,234 A | 4/1994 | Johnson | |
| 5,306,296 A | 4/1994 | Wright et al. | |
| 5,337,736 A | 8/1994 | Reddy | |
| 5,360,444 A | 11/1994 | Kusuhara | |
| 5,364,365 A | 11/1994 | Wortrich | |
| 5,364,393 A | 11/1994 | Auth et al. | |
| 5,429,131 A | 7/1995 | Scheinman et al. | |
| 5,450,860 A | 9/1995 | O'Connor | |
| 5,452,513 A | 9/1995 | Zinnbauer et al. | |
| 5,464,023 A | 11/1995 | Viera | |
| 5,545,178 A | 8/1996 | Kensey et al. | |
| 5,565,122 A | 10/1996 | Zinnbauer et al. | |
| 5,571,215 A | 11/1996 | Sterman et al. | |
| 5,593,424 A | 1/1997 | Northrup | |
| 5,607,471 A | 3/1997 | Seguin et al. | |
| 5,623,943 A | 4/1997 | Hackett et al. | |
| 5,626,590 A | 5/1997 | Wilk | |
| 5,640,955 A | 6/1997 | Ockuly et al. | |
| 5,656,028 A | 8/1997 | Swartz et al. | |
| 5,669,919 A | 9/1997 | Sanders et al. | |
| 5,674,279 A | 10/1997 | Wright et al. | |
| 5,682,906 A | 11/1997 | Sterman et al. | |
| 5,690,656 A | 11/1997 | Cope et al. | |
| 5,706,827 A | 1/1998 | Ehr et al. | |
| 5,713,907 A * | 2/1998 | Hogendijk | A61F 2/95 606/108 |
| 5,716,367 A | 2/1998 | Koike et al. | |
| 5,716,397 A | 2/1998 | Myers | |
| 5,716,399 A | 2/1998 | Love | |
| 5,776,080 A | 7/1998 | Thome et al. | |
| 5,776,189 A | 7/1998 | Khalid | |
| 5,797,939 A | 8/1998 | Yoon | |
| 5,813,996 A | 9/1998 | Sl. Germain et al. | |
| 5,824,066 A | 10/1998 | Gross | |
| 5,827,300 A | 10/1998 | Fleega | |
| 5,829,447 A | 11/1998 | Stevens et al. | |
| 5,830,224 A | 11/1998 | Cohn et al. | |
| 5,851,185 A | 12/1998 | Berns | |
| 5,860,920 A | 1/1999 | McGee et al. | |
| 5,868,733 A | 2/1999 | Ockuly et al. | |
| 5,879,366 A | 3/1999 | Shaw | |
| 5,888,240 A | 3/1999 | Carpentier et al. | |
| 5,906,579 A | 5/1999 | Vander Salm et al. | |
| 5,911,720 A | 6/1999 | Bourne et al. | |
| 5,928,224 A | 7/1999 | Laufer | |
| 5,931,818 A | 8/1999 | Werp et al. | |
| 5,944,738 A | 8/1999 | Amplatz et al. | |
| 5,967,984 A | 10/1999 | Chu et al. | |
| 5,980,515 A | 11/1999 | Tu | |
| 5,984,939 A | 11/1999 | Yoon | |
| 6,015,414 A | 1/2000 | Werp et al. | |
| 6,027,514 A | 2/2000 | Stine et al. | |
| 6,042,581 A | 3/2000 | Ryan et al. | |
| 6,050,472 A | 4/2000 | Shibata | |
| 6,050,936 A | 4/2000 | Schweich, Jr. et al. | |
| 6,068,637 A | 5/2000 | Popov et al. | |
| 6,068,648 A | 5/2000 | Cole et al. | |
| 6,071,292 A | 6/2000 | Makower et al. | |
| 6,099,460 A | 8/2000 | Denker | |
| 6,102,945 A | 8/2000 | Campbell | |
| 6,113,611 A | 9/2000 | Allen et al. | |
| 6,126,647 A | 10/2000 | Posey et al. | |
| RE36,974 E | 11/2000 | Bonutti | |
| 6,159,234 A | 12/2000 | Bonutti et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,183 A | 12/2000 | Kuehn et al. | |
| 6,173,199 B1 | 1/2001 | Gabriel | |
| 6,190,353 B1 | 2/2001 | Makower et al. | |
| 6,197,017 B1 | 3/2001 | Brock et al. | |
| 6,206,895 B1 | 3/2001 | Levinson | |
| 6,210,432 B1 | 4/2001 | Solem et al. | |
| 6,231,587 B1 | 5/2001 | Makower | |
| 6,267,781 B1 | 7/2001 | Tu | |
| 6,269,819 B1 | 8/2001 | Oz et al. | |
| 6,285,903 B1 | 9/2001 | Rosenthal et al. | |
| 6,287,317 B1 | 9/2001 | Makower et al. | |
| 6,298,257 B1 | 10/2001 | Hall et al. | |

(56) References Cited

U.S. PATENT DOCUMENTS

| | | |
|---|---|---|
| 6,306,133 B1 | 10/2001 | Tu et al. |
| 6,312,447 B1 | 11/2001 | Grimes |
| 6,319,263 B1 | 11/2001 | Levinson |
| 6,332,089 B1 | 12/2001 | Acker et al. |
| 6,332,893 B1 | 12/2001 | Mortier et al. |
| 6,352,543 B1 | 3/2002 | Cole |
| 6,385,472 B1 | 5/2002 | Hall et al. |
| 6,401,720 B1 | 6/2002 | Stevens et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,447,522 B2 | 9/2002 | Gambale et al. |
| 6,461,366 B1 * | 10/2002 | Seguin ............ A61B 17/00234 606/139 |
| 6,500,184 B1 | 12/2002 | Chan et al. |
| 6,524,303 B1 | 2/2003 | Garibaldi |
| 6,530,952 B2 | 3/2003 | Vesely |
| 6,537,198 B1 | 3/2003 | Vidlund et al. |
| 6,537,314 B2 | 3/2003 | Langberg et al. |
| 6,542,766 B2 | 4/2003 | Hall et al. |
| 6,544,230 B1 | 4/2003 | Flaherty et al. |
| 6,554,852 B1 | 4/2003 | Oberlander |
| 6,561,019 B1 | 5/2003 | Sell |
| 6,562,019 B1 | 5/2003 | Sell |
| 6,565,562 B1 | 5/2003 | Shah et al. |
| 6,589,208 B2 | 7/2003 | Ewers et al. |
| 6,594,517 B1 | 7/2003 | Nevo |
| 6,596,014 B2 | 7/2003 | Levinson et al. |
| 6,619,291 B2 | 9/2003 | Hlavka et al. |
| 6,626,919 B1 | 9/2003 | Swanstrom |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,655,386 B1 | 12/2003 | Makower et al. |
| 6,656,221 B2 | 12/2003 | Taylor et al. |
| 6,669,687 B1 | 12/2003 | Saadat |
| 6,669,707 B1 | 12/2003 | Swanstrom et al. |
| 6,676,702 B2 | 1/2004 | Mathis |
| 6,689,164 B1 | 2/2004 | Sequin |
| 6,699,263 B2 | 3/2004 | Cope |
| 6,702,825 B2 | 3/2004 | Frazier et al. |
| 6,702,826 B2 | 3/2004 | Liddicoat et al. |
| 6,718,985 B2 | 4/2004 | Hlavka et al. |
| 6,723,038 B1 | 4/2004 | Schroeder et al. |
| 6,730,112 B2 | 5/2004 | Levinson |
| 6,733,509 B2 | 5/2004 | Nobles et al. |
| 6,736,808 B1 | 5/2004 | Motamedi et al. |
| 6,746,472 B2 | 6/2004 | Frazier et al. |
| 6,764,500 B1 | 7/2004 | Muijs Van De Moer et al. |
| 6,769,434 B2 | 8/2004 | Liddicoat et al. |
| 6,793,618 B2 | 9/2004 | Schweich, Jr. et al. |
| 6,866,673 B2 | 3/2005 | Oren et al. |
| 6,913,608 B2 | 7/2005 | Liddicoat et al. |
| 6,921,407 B2 | 7/2005 | Nguyen et al. |
| 6,923,823 B1 | 8/2005 | Bartlett et al. |
| 6,942,694 B2 | 9/2005 | Liddicoat et al. |
| 6,945,978 B1 | 9/2005 | Hyde |
| 6,949,122 B2 | 9/2005 | Adams et al. |
| 6,964,674 B1 | 11/2005 | Matsuura et al. |
| 6,964,683 B2 | 11/2005 | Kowalsky et al. |
| 7,004,958 B2 | 2/2006 | Adams et al. |
| 7,037,334 B1 | 5/2006 | Hlavka et al. |
| 7,101,395 B2 | 9/2006 | Tremulis et al. |
| 7,166,127 B2 | 1/2007 | Spence et al. |
| 7,211,094 B2 | 5/2007 | Gannoe et al. |
| 2001/0005787 A1 | 6/2001 | Oz et al. |
| 2001/0039436 A1 | 11/2001 | Frazier et al. |
| 2001/0049492 A1 | 12/2001 | Frazier et al. |
| 2002/0013571 A1 | 1/2002 | Goldfarb et al. |
| 2002/0016628 A1 | 2/2002 | Langberg et al. |
| 2002/0026198 A1 | 2/2002 | Ockuly et al. |
| 2002/0026216 A1 | 2/2002 | Grimes |
| 2002/0029080 A1 | 3/2002 | Mortier et al. |
| 2002/0042621 A1 | 4/2002 | Liddicoat et al. |
| 2002/0072758 A1 | 6/2002 | Reo et al. |
| 2002/0087169 A1 | 7/2002 | Brock et al. |
| 2002/0087173 A1 | 7/2002 | Alferness et al. |
| 2002/0087178 A1 | 7/2002 | Nobles et al. |
| 2002/0095167 A1 | 7/2002 | Liddicoat et al. |
| 2002/0100485 A1 | 8/2002 | Stevens et al. |
| 2002/0103532 A1 | 8/2002 | Langberg et al. |
| 2002/0107531 A1 | 8/2002 | Schreck et al. |
| 2002/0128708 A1 | 9/2002 | Northrup, III et al. |
| 2002/0143383 A1 | 10/2002 | Parodi |
| 2002/0156526 A1 | 10/2002 | Hlavka et al. |
| 2002/0165535 A1 | 11/2002 | Lesh et al. |
| 2002/0169359 A1 | 11/2002 | McCarthy et al. |
| 2002/0169502 A1 | 11/2002 | Mathis |
| 2002/0169504 A1 | 11/2002 | Alferness et al. |
| 2002/0173841 A1 | 11/2002 | Ortiz et al. |
| 2002/0183766 A1 | 12/2002 | Seguin |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0078671 A1 | 4/2003 | Lesniak et al. |
| 2003/0083538 A1 | 5/2003 | Adams et al. |
| 2003/0083560 A1 | 5/2003 | Osypka |
| 2003/0105474 A1 | 6/2003 | Bonutti |
| 2003/0105520 A1 | 6/2003 | Alferness et al. |
| 2003/0120340 A1 | 6/2003 | Liska et al. |
| 2003/0130730 A1 | 7/2003 | Cohn et al. |
| 2003/0144697 A1 | 7/2003 | Mathis et al. |
| 2003/0160721 A1 | 8/2003 | Gilboa et al. |
| 2003/0171776 A1 | 9/2003 | Adams et al. |
| 2003/0171806 A1 | 9/2003 | Mathis et al. |
| 2003/0199974 A1 | 10/2003 | Lee et al. |
| 2003/0208195 A1 | 11/2003 | Thompson et al. |
| 2003/0212453 A1 | 11/2003 | Mathis et al. |
| 2003/0220685 A1 | 11/2003 | Hlavka et al. |
| 2003/0233038 A1 | 12/2003 | Hassett |
| 2003/0233142 A1 | 12/2003 | Morales et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | Sl. Goar et al. |
| 2004/0039442 A1 | 2/2004 | Sl. Goar et al. |
| 2004/0044364 A1 | 3/2004 | DeVries et al. |
| 2004/0049211 A1 | 3/2004 | Tremulis et al. |
| 2004/0092962 A1 | 5/2004 | Thornton et al. |
| 2004/0093023 A1 | 5/2004 | Allen et al. |
| 2004/0097865 A1 | 5/2004 | Anderson et al. |
| 2004/0122456 A1 | 6/2004 | Saadat et al. |
| 2004/0127983 A1 | 7/2004 | Mortier et al. |
| 2004/0133063 A1 | 7/2004 | McCarthy et al. |
| 2004/0147958 A1 | 7/2004 | Lam et al. |
| 2004/0152947 A1 | 8/2004 | Schroeder et al. |
| 2004/0162568 A1 | 8/2004 | Saadat et al. |
| 2004/0167539 A1 | 8/2004 | Kuehn et al. |
| 2004/0167620 A1 | 8/2004 | Ortiz et al. |
| 2004/0172046 A1 * | 9/2004 | Hlavka ............ A61B 17/00234 606/142 |
| 2004/0186486 A1 | 9/2004 | Roue et al. |
| 2004/0186566 A1 | 9/2004 | Hindichs et al. |
| 2004/0193191 A1 | 9/2004 | Starksen et al. |
| 2004/0220473 A1 | 11/2004 | Lualdi |
| 2004/0236419 A1 | 11/2004 | Milo |
| 2004/0243153 A1 | 12/2004 | Liddicoat et al. |
| 2004/0243227 A1 | 12/2004 | Starksen et al. |
| 2004/0260317 A1 | 12/2004 | Bloom et al. |
| 2005/0033446 A1 | 2/2005 | Deem et al. |
| 2005/0049681 A1 | 3/2005 | Greenhalgh et al. |
| 2005/0055087 A1 | 3/2005 | Starksen |
| 2005/0055089 A1 | 3/2005 | Macoviak et al. |
| 2005/0065550 A1 | 3/2005 | Starksen et al. |
| 2005/0065601 A1 | 3/2005 | Lee et al. |
| 2005/0075723 A1 | 4/2005 | Schroeder et al. |
| 2005/0107810 A1 | 5/2005 | Morales et al. |

(56) References Cited

U.S. PATENT DOCUMENTS

| | | |
|---|---|---|
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0119735 A1 | 6/2005 | Spence et al. |
| 2005/0125011 A1 | 6/2005 | Spence |
| 2005/0131438 A1 | 6/2005 | Cohn |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0216039 A1 | 9/2005 | Lederman |
| 2005/0234481 A1 | 10/2005 | Waller |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267533 A1 | 12/2005 | Gertner |
| 2005/0267571 A1 | 12/2005 | Spence et al. |
| 2005/0283192 A1 | 12/2005 | Torrie et al. |
| 2005/0288694 A1 | 12/2005 | Solomon |
| 2006/0004410 A1 | 1/2006 | Nobis et al. |
| 2006/0009784 A1 | 1/2006 | Behl et al. |
| 2006/0020319 A1* | 1/2006 | Kim .................. A61F 2/07 623/1.11 |
| 2006/0069429 A1 | 3/2006 | Spence et al. |
| 2006/0142756 A1 | 6/2006 | Davies et al. |
| 2006/0178682 A1 | 8/2006 | Boehlke |
| 2006/0212045 A1 | 9/2006 | Schilling et al. |
| 2007/0010857 A1 | 1/2007 | Sugimoto et al. |
| 2007/0080188 A1 | 4/2007 | Spence et al. |
| 2007/0106310 A1 | 5/2007 | Goldin et al. |
| 2007/0112424 A1 | 5/2007 | Spence et al. |
| 2008/0228165 A1 | 9/2008 | Spence et al. |
| 2008/0228198 A1 | 9/2008 | Traynor et al. |
| 2008/0228266 A1 | 9/2008 | McNamara et al. |
| 2008/0228267 A1 | 9/2008 | Spence et al. |
| 2008/0275503 A1 | 11/2008 | Spence et al. |

FOREIGN PATENT DOCUMENTS

| | | |
|---|---|---|
| WO | WO 99/00059 | 1/1999 |
| WO | WO 00/03759 | 1/2000 |
| WO | WO 0044311 | 8/2000 |
| WO | WO 0060995 | 10/2000 |
| WO | WO 0067640 | 11/2000 |
| WO | WO 0200099 | 1/2002 |
| WO | WO 02051329 | 7/2002 |
| WO | WO 02096275 | 12/2002 |
| WO | WO 03/001893 | 1/2003 |
| WO | WO 03007796 | 1/2003 |
| WO | WO 03/053289 | 7/2003 |
| WO | WO 2004/045378 | 6/2004 |
| WO | WO 2004/112658 | 12/2004 |
| WO | WO 2005011463 | 2/2005 |
| WO | WO 2005013832 | 2/2005 |
| WO | WO 2005/025644 | 3/2005 |
| WO | WO 2006064490 | 6/2006 |
| WO | WO 2007005394 | 1/2007 |

OTHER PUBLICATIONS

F. Maisano et al., The Double-Orifice Technique as a Standardized Approach to Treat Mitral Regurgitation Due to Severe Myxomatous Disease: Surgical Technique, European Journal of Cardio-thoracis Surgery, 1998.

Douglas P. Zipes, MD et al., Ablation of Free Wall Accessory Pathways, Catheter Ablation of Arrhythmias, Chapter 8, 7 pgs., 1994.

Zsolt L. Nagy et al., Mitral Annuloplasty with a Suture Technique, European Journal of Cardio-thoracic Surgery 18, Aug. 15, 2000, 1 pg.

David L.S. Morales et al., Development of an Off Bypass Mitral Valve Repair, Department of Surgery, Columbia University, College of Physicians and Surgeons, New York, NY.

Heart Surgery Forum, Aug. 8, 2000. Page 1. Tables 1-2,Web, http://www.hsforum.com/vol2/issue2/1999-4963 tables.html>.

Heart Surgery Forum, Aug. 8, 2000. Pages 1-4. Figures 1-8.Web. http://www.hsforum.com1vol2/issue2/1999-4963figures.html>.

"Heart Valves: The Duran Flexible Annuloplasty Band—for Surgeons "Partial" to Flexiblity." Medtronic. Feb. 23, 2001. Web. http://medtronic.com/cardiac/heartvalves/duran_band/>.

* cited by examiner

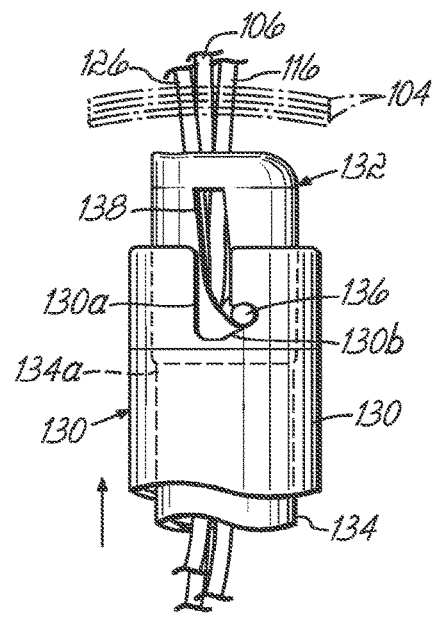 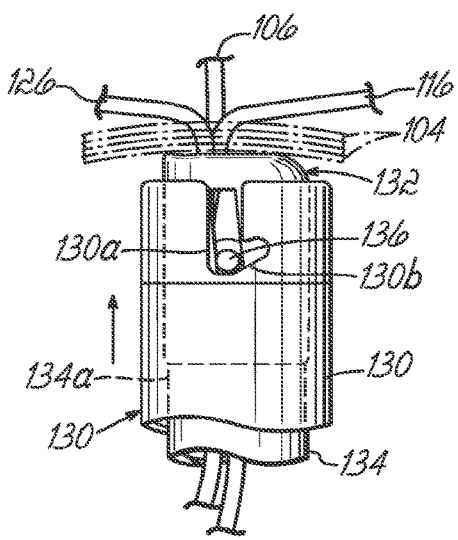
FIG. 16A    FIG. 16B
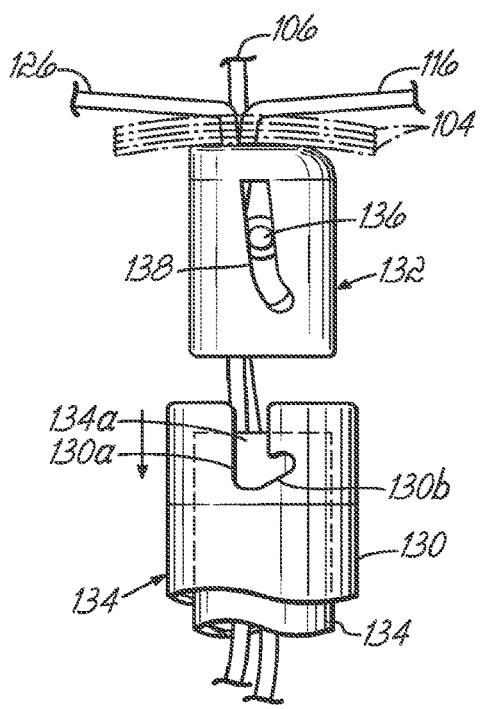 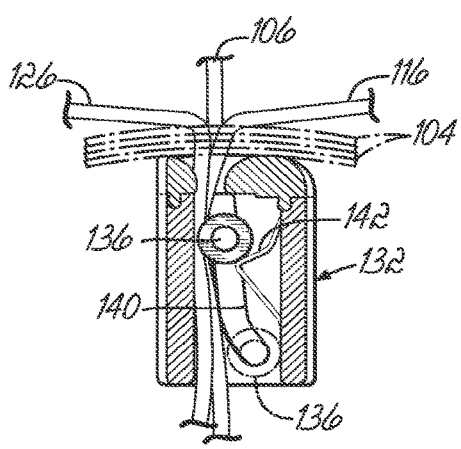
FIG. 16C    FIG. 16D

SYSTEMS AND METHODS FOR INTRODUCING ELEMENTS INTO TISSUE

CROSS-REFERENCE TO RELATED APPLICATIONS

The present application is a divisional of U.S. patent application Ser. No. 11/685,239, filed Mar. 13, 2007, now U.S. Pat. No. 8,845,723, issued Sep. 30, 2014, which is hereby incorporated by reference in its entirety.

TECHNICAL FIELD

The present invention relates generally to tissue fastening and, more particularly, tissue fastening performed in a minimally invasive and percutaneous manner.

BACKGROUND

Referring initially to FIGS. 1-4 solely for purposes of understanding the anatomy of a heart 10, and specifically the left side of the heart 10, the left atrium (LA) 12 and left ventricle (LV) 14 are shown. An aorta 16 receives oxygenated blood from left ventricle 14 through an aortic valve 18, which serves to prevent regurgitation of blood back into left ventricle 14. A mitral valve 20 is positioned between left atrium 12 and left ventricle 14, and allows one-way flow of the oxygenated blood from the left atrium 12 to the left ventricle 14.

Mitral valve 20, which will be described below in more detail, includes an anterior leaflet 22 and a posterior leaflet 24 that are coupled to cordae tendonae 26, 28 (FIG. 4). Cordea tendonea 26, 28 serve as "tension members" that prevent the leaflets 22, 24 of mitral valve 20 from moving past their closing point and prolapsing back into the left atrium 12. When left ventricle 14 contracts during systole, cordae tendonae 26, 28 limit the upward motion (toward the left atrium) of the anterior and posterior leaflets 22, 24 past the point at which the anterior and posterior leaflets 22, 24 meet and seal to prevent backflow from the left ventricle 14 to the left atrium 12 ("mitral regurgitation" or "mitral insufficiency"). Cordae tendonae 26, 28 arise from a columnae carnae or, more specifically, a musculi papillares (papillary muscles) of the columnae carnae. In various figures herein, some anatomical features have been deleted solely for clarity.

Anterior leaflet 22 and posterior leaflet 24 of the mitral valve 20 are generally thin, flexible membranes. When mitral valve 20 is closed, anterior leaflet 22 and posterior leaflet 24 are generally aligned and contact one another along a "line of coaptation" several millimeters back from their free edges, to create a seal that prevents mitral regurgitation. Alternatively, when mitral valve 20 is opened, blood flows downwardly through an opening created between anterior leaflet 22 and posterior leaflet 24 into left ventricle 14.

Many problems relating to the mitral valve may occur and may cause many types of ailments. Such problems include, but are not limited to, mitral regurgitation. Mitral regurgitation, or leakage, is the backflow of blood from left ventricle 14 into the left atrium 12 due to an imperfect closure of mitral valve 20. That is, leakage often occurs when the anterior and posterior leaflets 22, 24 do not seal against each other, resulting in a gap between anterior leaflet 22 and posterior leaflet 24 when the leaflets are supposed to be fully coapted during systole.

In general, a relatively significant systolic gap may exist between anterior leaflet 22 and posterior leaflet 24 for a variety of different reasons. For example, a gap may exist due to congenital malformations, because of ischemic disease, or because the heart 10 has been damaged by a previous heart attack. Such a gap may also be created when congestive heart failure, e.g., cardiomyopathy, or some other type of distress which causes a heart 10 to be enlarged. Enlargement of the heart 10 can result in dilation (stretching) of the mitral annulus. This enlargement is usually limited to the posterior valve annulus and is associated with the posterior leaflet 24, because the anterior annulus is a relatively rigid fibrous structure. When the posterior annulus enlarges, it causes the posterior leaflet 24 to move away from the anterior leaflet 22, causing a gap during systole because the two leaflets no longer form proper coaptation. This results in leakage of blood through the valve 20, or regurgitation.

Blood leakage through mitral valve 20 generally causes a heart 10 to operate less efficiently, as the heart 10 pumps blood both out to the body via the aorta 16, and also back (in the form of mitral regurgitation) into the left atrium 12. Leakage through mitral valve 20, or general mitral insufficiency, is thus often considered to be a precursor to congestive heart failure (CHF) or a cause of progressive worsening of heart failure. There are generally different levels of symptoms associated with heart failure. These levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort and has symptoms of cardiac insufficiency even at rest. In general, correcting or reducing the degree of mitral valve leakage may be successful in allowing the NYHA classification grade of a patient to be reduced. For instance, a patient with a Class 4 classification may have his classification reduced to Class 3 or Class 2 and, hence, be relatively comfortable at rest or even during mild physical exertion. By eliminating the flow of blood backwards into the left atrium 12, therapies that reduce mitral insufficiency reduce the workload of the heart 10 and may prevent or slow the degradation of heart function and congestive heart failure symptoms that is common when a significant degree of mitral insufficiency remains uncorrected.

Treatments used to correct for mitral valve leakage or, more generally, CHF, are typically highly invasive, open-heart surgical procedures. In extreme cases, this may include implantation of a ventricular assist device such as an artificial heart in a patient with a failing heart. The implantation of a ventricular assist device is often expensive, and a patient with a ventricular assist device must be placed on extended anti-coagulant therapy. Anti-coagulant therapy reduces the risk of blood clot formation for example, within the ventricular assist device. Reducing the risks of blood clots associated with the ventricular assist device is desirable, but anti-coagulant therapies may increase the risk of uncontrollable bleeding in a patient, e.g., as a result of a fall.

Rather than implanting a ventricular assist device, bi-ventricular pacing devices similar to pacemakers may be implanted in some cases, e.g., cases in which a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive, and is generally not effective in significantly reducing or eliminating the degree of mitral regurgitation.

Open-heart surgical procedures that are intended to correct for mitral valve leakage, specifically, can involve the implantation of a replacement valve. Valves from animals, e.g., pigs, may be used to replace a mitral valve 20 in a human. While a pig valve may relatively successfully replace a mitral valve, such replacement valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

A less invasive surgical procedure involves heart bypass surgery associated with a port access procedure. For a port access procedure, the heart may be accessed by cutting between ribs or sometimes removing parts of one or more ribs, as opposed to dividing the sternum to open the entire chest of a patient.

One open-heart surgical procedure that is particularly successful in correcting for mitral valve leakage and, in addition, mitral regurgitation, is an annuloplasty procedure. During an annuloplasty procedure, a medical device such as an annuloplasty ring may be implanted surgically on the left atrial side of mitral annulus (i.e., generally the attachment location of the base of the mitral valve to the heart). The device reduces a dilated mitral valve annulus to a relatively normal size and, specifically, moves the posterior leaflet closer to the anterior leaflet to aid anterior—posterior leaflet coaptation and thus improve the quality of mitral valve closure during systole. Annuloplasty rings are often shaped substantially like the letter "D" to correspond to the natural shape of the mitral annulus as viewed from above. Typically, the rings are formed from a rod or tube of biocompatible material, e.g., plastic, that has a DACRON mesh covering.

In order for an annuloplasty ring to be implanted, a surgeon surgically attaches the annuloplasty ring to the mitral valve on the atrial side of the mitral valve. Conventional methods for installing a ring require open-heart surgery which involves opening a patient's sternum and placing the patient on a heart bypass machine. The annuloplasty ring is sewn on a top portion of the mitral valve. In sewing the annuloplasty ring onto the mitral valve, a surgeon generally sews the straight side of the "D" to the fibrous tissue located at the junction between the posterior wall of the aorta and the base of the anterior mitral valve leaflet. As the curved part of the ring is sewn to the posterior aspect of the annulus, the surgeon alternately acquires a relatively larger amount of tissue from the mitral annulus, e.g., a one-eighth inch bite of tissue, using a needle and thread, compared to a relatively smaller bite taken of the fabric covering of the annuloplasty ring. Once the thread has loosely coupled the annuloplasty ring to the mitral valve annulus tissue, the annuloplasty ring is slid into contact with the mitral annulus. The tissue of the posterior mitral annulus that was previously stretched out, e.g., due to an enlarged heart, is effectively reduced in circumference and pulled forwards towards the anterior mitral leaflet by the tension applied by annuloplasty ring with the suture or thread. As a result, a gap between anterior leaflet 22 and posterior leaflet 24 during ventricular contraction or systole may be reduced and even substantially closed off in many cases thereby significantly reducing or even eliminating mitral insufficiency. After the mitral valve 20 is shaped by the ring, the anterior and posterior leaflets 22, 24 will reform typically by pulling the posterior leaflet 24 forward to properly meet the anterior leaflet 22 and create a new contact line that will enable mitral valve 20 to appear and to function properly.

Although a patient that receives an annuloplasty ring may be subjected to anti-coagulant therapies, the therapies are not extensive, as a patient is only subjected to the therapies for a matter of weeks, e.g., until tissue grows over the annuloplasty ring.

Another type of procedure that is generally effective in reducing mitral valve leakage associated with prolapse of the valve leaflets involves placing a single edge-to-edge suture in the mitral valve 20 that apposes the mid-portions of anterior and posterior leaflets 22, 24. For example, in an Alfieri stitch or a bow-tie repair procedure, an edge-to-edge stitch is made at approximately the center of the gap between an anterior leaflet 22 and a posterior leaflet 24 of a mitral valve 20. Once the stitch is in place between the anterior and posterior leaflets 22, 24, it is pulled in to form a suture which holds anterior leaflet 22 against posterior leaflet 24.

Another surgical procedure that reduces mitral valve leakage involves placing sutures along a mitral valve annulus around the posterior leaflet 24. These sutures may be formed as a double track, e.g., in two "rows" from a single strand of suture material. The sutures are tied off at approximately a central point (P2) of posterior leaflet 24. Pledgets are often positioned under selected sutures to prevent the sutures from tearing through annulus 40. When the sutures are tightened and tied off, the circumference of the annulus 40 may effectively be reduced to a desired size such that the size of a systolic gap between posterior leaflet 24 and an anterior leaflet 22 may be reduced.

While invasive surgical procedures have proven to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits. Further, given the complexity of open-heart surgery, and the significant associated recovery time, people that are not greatly inconvenienced by CHF symptoms, e.g., people at a Class 1 classification, may choose not to have corrective surgery. In addition, people that need open heart surgery the most, e.g., people at a Class 4 classification, may either be too frail or too weak to undergo the surgery. Hence, many people that may benefit from a surgically repaired mitral valve may not undergo surgery.

In another method, a cinching device is placed within the coronary sinus (CS) using a catheter system, with distal, mid, and proximal anchors within the lumen of the CS to allow plication of the annulus 40 via the CS. In practice, these anchors are cinched together and the distance between them is shortened by pulling a flexible tensile member such as a cable or suture with the intent being to shorten the valve annulus 40 and pull the posterior leaflet 24 closer to the anterior leaflet 22 in a manner similar to an annuloplasty procedure. Unfortunately, since the tissue that forms the CS is relatively delicate, the anchors are prone to tear the tissue during the cinching procedure. In addition, the effect on the mitral annulus may be reduced when the CS of a particular patient is not directly aligned with the mitral annulus. Other minimally invasive techniques have been proposed but have various drawbacks related to such factors as effectiveness and/or accuracy of catheter-based implementation.

SUMMARY

In one embodiment, a system is provided for accurately introducing an element into tissue proximate (i.e., either at or close to) the mitral valve annulus of the heart of a patient. The element may be any desired structure suitable for the intended purpose. In one more specific embodiment, for example, the element may advantageously comprise a guide wire. The system includes a first catheter device having a first distal end portion capable of being introduced through the vascular system of the patient and into the coronary sinus proximate the mitral valve annulus. The first catheter device includes first, second and third spaced apart radiopaque markers at the first distal end portion. The system further includes a second catheter device having a second distal end portion capable of being introduced through the vascular system of the patient and into the left ventricle of the heart proximate the mitral valve annulus. The second catheter device includes a fourth radiopaque marker at the second distal end portion and a lumen for delivering an element from the second distal end portion. The fourth radiopaque marker may be aligned with reference to at least one of the first, second or third radiopaque markers to deliver the element into the mitral valve tissue. In one exemplary embodiment, for example, the fourth radiopaque marker is aligned with the first radiopaque marker of the first catheter device generally at location P2 of the posterior mitral annulus. The first, second and third radiopaque markers may be spaced apart to correspond to locations P1, P2 and P3 of the posterior mitral valve annulus.

A method is also provided for accurately introducing an element into tissue proximate the mitral valve annulus using a first catheter device having a first distal end portion with a first radiopaque marker and a second catheter device having a second distal end portion with a lumen. The method comprises introducing the first distal end portion of the first catheter device through the vascular system of the patient and into the coronary sinus proximate the mitral valve annulus. The first radiopaque marker is positioned at a desired location in the coronary sinus proximate the mitral valve annulus. The second distal end portion of the second catheter device is introduced through the vascular system of the patient and into the heart proximate the mitral valve annulus. The second distal end portion is positioned in a desired orientation relative to the first radiopaque marker. The element is then delivered through the lumen into tissue proximate the mitral valve annulus with the second distal end portion in the desired orientation.

The method of accurately introducing the element into tissue proximate the mitral valve annulus may further comprise delivering a first guide wire through the mitral valve annulus and into the left atrium of the heart from the left ventricle of the heart. The method may further comprise guiding a second element over the first guide wire to a position proximate the mitral valve annulus and the second element may further comprise a third catheter device. A second guide wire may be delivered from the third catheter device through the mitral valve annulus and into the left atrium of the heart from the left ventricle of the heart. The method may further comprise using the first and second guide wires to deliver first and second anchors, respectively, into the mitral valve annulus, shortening the distance between the first and second anchors, and locking the first and second anchors with respect to each other. This may, for example, form plicated annulus tissue helpful for reducing regurgitation through the mitral valve. A third guide wire may be delivered from the third catheter device through the mitral valve annulus and into the left atrium of the heart from the left ventricle of the heart. This third guide wire may be used to deliver a third anchor into the mitral valve annulus and the distance between at least two of the first, second or third anchors may be shortened and then at least these two anchors may be locked with respect to each other. In an illustrative embodiment, all three anchors are locked with respect to each other with the tissue plicated between each of the adjacent anchors. The first distal end portion may further comprise two additional radiopaque markers spaced apart on opposite sides of the first radiopaque marker. In this case, the method may further comprise positioning the first radiopaque marker at a location in the coronary sinus proximate location P2 of the mitral valve annulus, and positioning the two additional radiopaque markers in the coronary sinus respectively more proximate to locations P1 and P3 of the mitral valve annulus. As further options, the second distal end portion may further include a second radiopaque marker and positioning the second distal end may further comprise positioning the second radiopaque marker in a desired orientation relative to the first radiopaque marker. The first radiopaque marker may have a predetermined cross sectional shape (e.g., circular) when viewed directly along the longitudinal axis of the first catheter device. In association with this feature, the method may further comprise viewing the first radiopaque marker directly along the longitudinal axis of the first catheter device while positioning the second distal end portion in the desired orientation.

In another illustrative embodiment, a catheter device is provided and capable of being directed through the vascular system of a patient and delivering first and second elements into tissue. Again, these elements may be any structure suited for the intended purpose. The catheter device comprises first, second and third catheter members respectively including first, second and third lumens. A first connecting member is coupled between the first and second catheter members and a second connecting member coupled between the first and third catheter members. The second and third catheter members are laterally movable in generally opposite directions relative to the first catheter member between collapsed positions suitable for delivery of the first, second and third catheter members through the vascular system and expanded positions in which the second and third catheter members are at laterally spaced apart positions relative to the first catheter member for delivering the first and second elements into the tissue through the second and third lumens.

The catheter device may further comprise a third connecting member coupled between the first and second catheter members and a fourth connecting member coupled between the first and third catheter members. The first, second, third and fourth connecting members may further comprise bars pivotally coupled between the first, second and third catheter members. The device may further comprise an outer catheter member or sheath having a fourth lumen with the fourth lumen receiving the first, second and third catheter members. In this embodiment, the first, second and third catheter members may therefore be a triple lumen catheter received within and extendable from the distal end of an outer sheath. The second and third catheter members may be movable in a lengthwise direction relative to the first catheter member as the second and third catheter members move laterally to the expanded positions.

The catheter device including the triple lumen catheter, or first, second and third catheter members, may further comprise first, second and third guide wires respectively received in the first, second and third lumens. For example, the first guide wire may be used as an initial guide for delivery of the catheter device to a surgical site, such as within the left ventricle of the heart, and the second and third guide wires may be extendable from the device into tissue, such as mitral valve annulus tissue. The first, second and third guide wires may further comprise radiofrequency (RF) energy delivery wires capable of applying radiofrequency energy to assist with penetrating the tissue.

In another embodiment, a method is provided for delivering respective elements into spaced apart locations along an annulus of a mitral valve using a catheter device including first, second and third catheter members that respectively include first, second and third lumens. The method comprises directing a first guide wire through the vascular system and into the heart of a patient. The first, second and third catheter members are introduced through the vascular system and into the heart of the patient with the first guide wire received in the first lumen and with the first, second and third catheter members are in a collapsed state relative to one another. Distal end portions of the first, second and third catheter members are positioned proximate the annulus. The distal end portions of the second and third catheter members are expanded laterally away from the first catheter member. The respective elements are then delivered respectively into tissue proximate the annulus through the second and third lumens.

The method of delivering respective elements into spaced apart locations along the annulus may further comprise delivering second and third guide wires respectively through the second and third lumens. The method may further comprise applying radiofrequency energy with distal tip portions of the second and third guide wires to assist with penetrating through the tissue. The distal end portions of the first, second and third guide wires may be extended into the left atrium of the heart. The method may then further comprise delivering first, second and third anchors into the tissue using the first, second and third guide wires as guides to the spaced apart locations. The first, second and third anchors may be connected to the tissue. Distances between two or more of the anchors may be shortened and locked in position as generally described above. Respective first, second and third flexible tensile member portions may be coupled to the first, second and third anchors and locking the first, second and third anchors may further comprise locking at least two of the first, second or third flexible tensile member portions together. The flexible tensile member portions may be comprised of any suitable material having requisite strength, flexibility and biocompatibility. For this purpose, for example, any suitable suture material, which may be portions of the same suture material, or discrete and separate suture threads having respective free ends, may be used. The first, second and third anchors may be respectively secured to the first, second and third flexible tensile members to form first, second and third anchor assemblies. These anchor assemblies may be delivered to the spaced apart locations via at least one anchor delivery catheter. In an illustrative embodiment, these anchor assemblies are individually delivered to the left ventricle via individual, separate anchor delivery catheters.

In another embodiment, a tissue anchor is provided generally comprising a flexible tensile member and a plurality of discrete, flat flexible anchor elements coupled for movement along the flexible tensile member to form one illustrative embodiment of an anchor assembly. The flexible tensile member and at least one of the plurality of discrete, flat flexible anchor elements are capable of being inserted through tissue and of moving between an elongate configuration and a shortened configuration suitable for anchoring the assembly against at least one side of the tissue. This anchor assembly includes a proximal end portion, a distal end portion, and a compressible intermediate portion between the proximal and distal end portions. The compressible intermediate portion is compressible in that it may be shortened during an anchoring process. For example, it may comprise multiple anchor elements itself, or more simply a space between proximal and distal anchor elements connected by the flexible tensile member. The anchor elements can slide relative to the flexible tensile member and the flexible tensile member is capable of being pulled to cause the anchor elements to move relative to the flexible tensile member from the elongate configuration to the shortened configuration.

In this anchor assembly embodiment, the anchor elements may be formed from any suitable biocompatible material. For example, the material may be selected from at least one of natural fibers, synthetic fibers, polymers, metals or any combinations thereof (i.e., combinations with one another and/or with other materials). In one embodiment, the anchor elements are formed of material that promotes tissue ingrowth such that after implantation, the anchor assembly will be essentially covered by natural tissue of the patient. The flexible tensile member may comprise a suture having a suitable lock member, such as a simple slip knot for allowing the proximal end of the flexible tensile member to be pulled causing movement of the slip knot distally and resulting in compression or relative movement of two or more anchor elements toward each other. The flexible tensile member may extend through each of the anchor elements at multiple locations and one or more of the anchor elements and/or the flexible tensile member, or both, may have at least one radiopaque marker to allow visualization under a suitable viewing device such as a fluoroscope during and/or after the anchor installation procedure. In this embodiment the plurality of discrete, flat flexible anchor elements may have any suitable shape. The anchor elements are sufficiently flexible to allow contraction or folding into an anchor delivery catheter and subsequent expansion or unfolding after deployment from the anchor delivery catheter to provide a wider retaining surface against the tissue. A deploying device may be operatively associated with the anchor delivery catheter and operable to extend or deploy the anchor assembly from the anchor delivery catheter. For example, this deploying device may further comprise a deploying member, such as a flexible rod or inner deployment catheter, capable of pushing the anchor assembly at least partially out of the lumen of the anchor delivery catheter.

In another embodiment, a method is provided for anchoring tissue with a first anchor assembly comprised of a first plurality of discrete, flat flexible anchor elements. The first anchor assembly includes a proximal end portion, a distal end portion and a compressible intermediate portion located between the proximal and distal end portions and movable between an elongated configuration and a shortened configuration. The method comprises inserting at least one of the anchor elements through the tissue and pulling a first flexible tensile member coupled for sliding movement relative to the first plurality of discrete, flat flexible anchor elements. This draws the proximal and distal end portions of the first anchor assembly toward each other and compresses the intermediate portion into the shortened configuration with the assembly engaged against the tissue. The tissue may comprise the mitral valve annulus and the first anchor assembly may be engaged on opposite sides of the tissue, such as on opposite sides of the mitral valve annulus. The method may further comprise inserting second and even third anchor assemblies through the tissue at spaced apart locations from the first anchor assembly and drawing the two or three anchor assemblies toward each other to plicate the tissue whereupon the anchor assemblies are locked relative to each other to lock the plicated condition of the tissue. This procedure may, for example, be repeated any number of times to plicate the posterior portion of the mitral valve annulus for purposes of achieving annuloplasty.

In another embodiment, a suture cutter is provided for percutaneously cutting a suture located within a patient. The suture cutter may comprise an actuator for manipulation by a medical professional and an intermediate catheter portion operatively coupled to the actuator for insertion into the vascular system of the patient. A cutting assembly is operatively coupled to the intermediate catheter portion and the actuator. The cutting assembly includes a blade housing and a blade with a cutting edge mounted for movement in the blade housing. An adjustably sized cutting window is defined between the cutting edge and the blade housing and the cutting edge cuts a suture received inside of the cutting window as the cutting edge moves in the blade housing to reduce the size of the cutting window. In one embodiment, an anvil may be positioned on an opposite side of the cutting window from the cutting edge and the suture may be cut against the anvil. In another embodiment, a blade receiving slot may be located on an opposite side of the cutting window from the cutting edge and the suture may be cut as the blade moves into the blade receiving slot. The blade housing may further comprise a first aperture on one side of the blade and a second aperture on an opposite side of the blade such that the suture is adapted to pass from the first aperture to the second aperture through the cutting window.

In another embodiment, a method of cutting a suture located within a patient is provided and involves positioning a suture cutter within the patient, with the suture cutter including a blade movable through an adjustably sized cutting window. A suture is directed through the cutting window, such as at a time before the suture cutter is directed into the patient through the vascular system. The size of the cutting window is reduced by moving the blade towards the suture and the suture is then cut with the blade, either against an anvil or by directing the blade into a blade receiving space past the suture (e.g., into a slot). The suture cutter may be directed through a catheter leading into the vascular system of the patient. The suture cutter may be used, for example, to cut the tails from the sutures used during one or more of the annuloplasty procedures described herein.

In another embodiment, a plication assistance device is provided and may be used, for example, to tension and lock the flexible tensile members described herein. The device comprises a support structure and a first carriage fixed to the support structure and configured to hold an outer plication catheter, A second carriage is fixed to the support structure at a location proximal to the first carriage. At least one of the first or second carriages is slidable along the support structure and capable of being locked in position relative to the support structure. The second or proximal carriage is configured to hold an inner plication catheter. A first suture tensioning mechanism is mounted to the support structure at a location proximal to the second carriage and a second suture tensioning mechanism is mounted to the support structure also at a location proximal to the second carriage. The plication assistance device may further comprise a third suture tensioning mechanism mounted to the support structure at a location proximal to the second carriage. The first and second suture tensioning mechanisms may further comprise first and second rotatable spools. The first and second carriages may respectively include first and second locking devices for securing the outer plication catheter and inner plication catheter thereto. The plication assistance device may include a suture tension gauge operatively connected with the support structure and configured to measure tension of a suture being tensioned by at least one of the first or second suture tensioning mechanisms.

Various additional features, advantages, and aspects of the invention will become more readily apparent to those of ordinary skill in the art upon review of the following detailed description of the illustrative embodiments taken in conjunction with the accompanying drawings.

BRIEF DESCRIPTION OF THE DRAWINGS

FIGS. 16A, 16B and 16C are enlarged views showing the progressive deployment and locking of the suture locker onto the three sutures.

FIG. 16D is a longitudinal cross sectional view of the suture locker showing the locked condition.

DETAILED DESCRIPTION OF THE ILLUSTRATIVE EMBODIMENTS

Reference will be made to the various figures in describing the methods, devices and systems in various forms useful to the purpose of plicating tissue, for example, and particularly useful for plicating annulus tissue associated with the mitral valve of a patient. It will be appreciated that although specific details of the methods, devices and systems will be given herein, many different changes, substitutions and additions may be made to such details by those of ordinary skill while still falling within the inventive aspects more generally set forth herein and understood by those of ordinary skill upon review of the present disclosure in its entirety. It should be noted that the terms "proximal" and "distal" are used, as conventional in the art, to denote spatial relationship relative to the person using the particular device or component. That is, "proximal" refers to a position closer to the user and "distal" refers to a position farther from the user.

Figure 1:
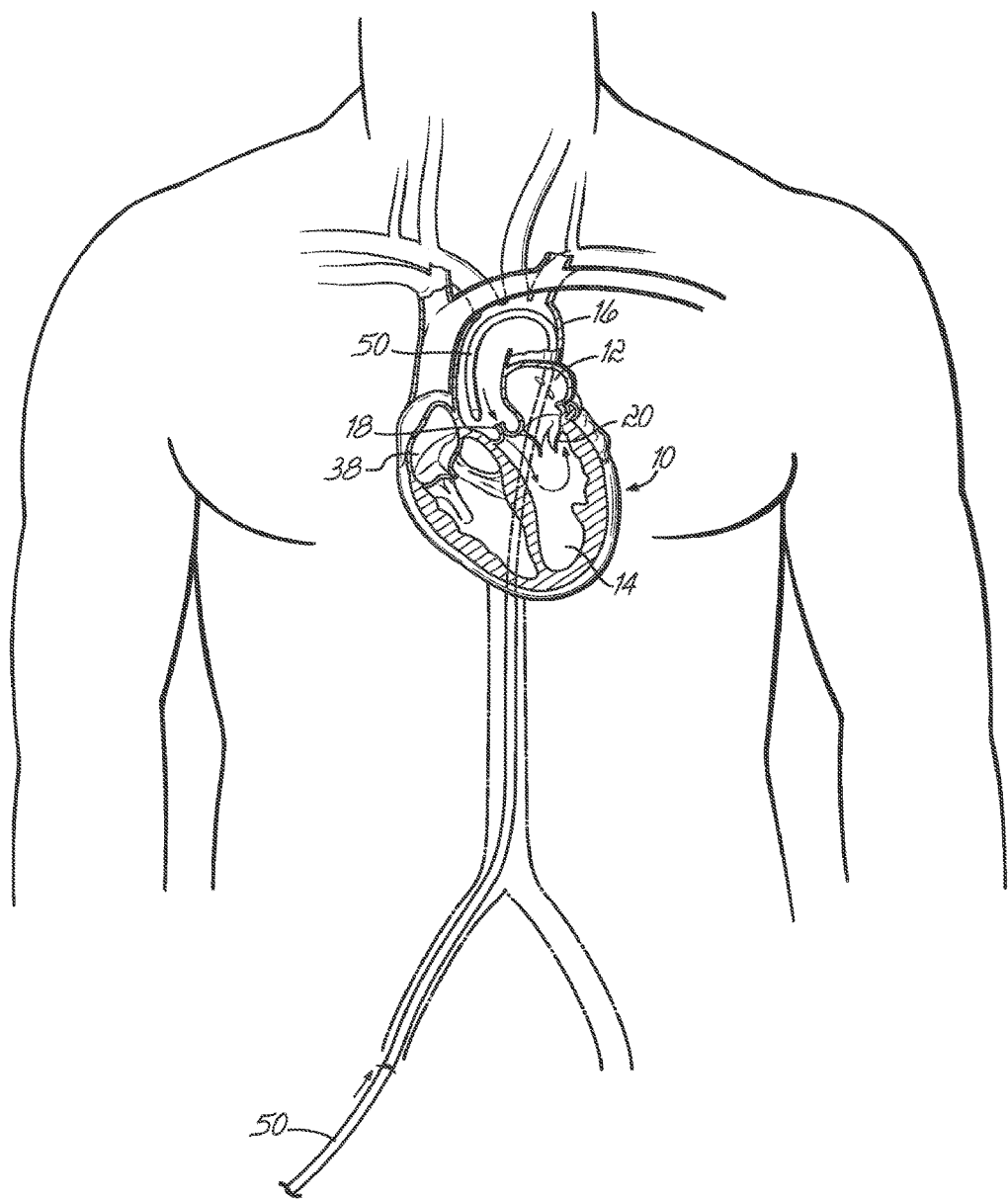
FIG. 1 is a schematic illustration of a patient with the anatomy of the heart in cross section and a guide catheter introduced through the vascular system into the aorta and heart of the patient.
Figure 2:
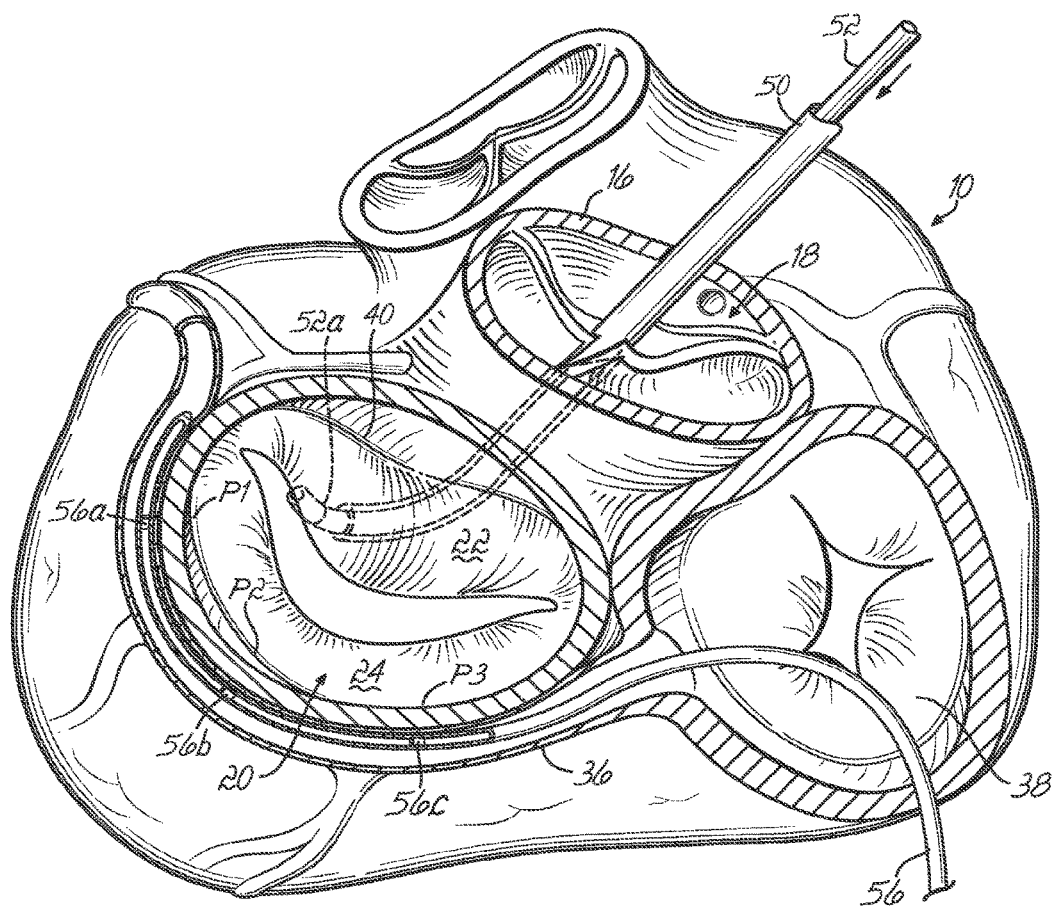
FIG. 2 is a cross sectional view of the heart from above showing the introduction of various catheters.
Figure 3:
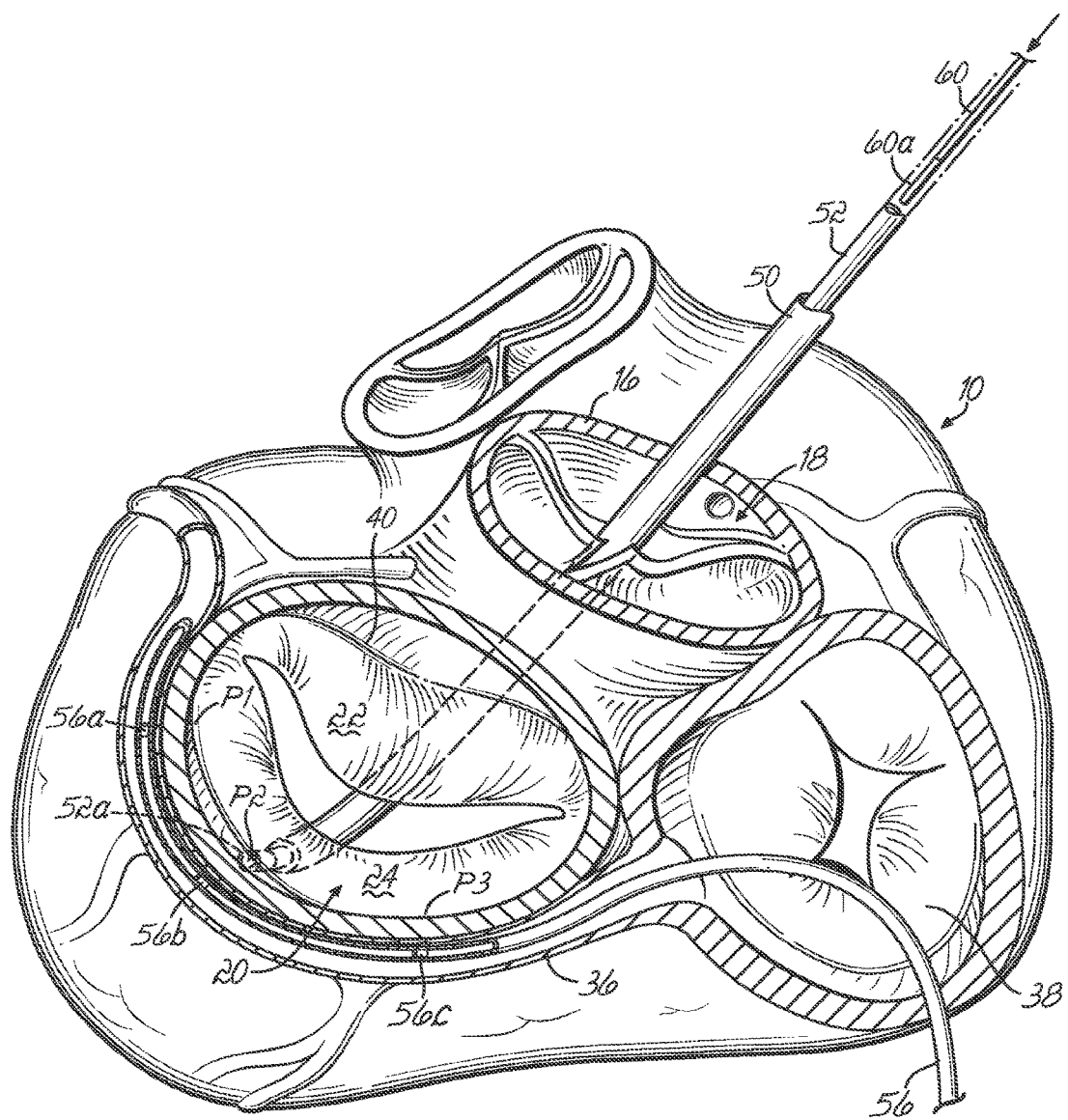
FIG. 3 is a cross sectional view of the heart similar to FIG. 2 and illustrating the further introduction of a guide wire.
Figure 4:
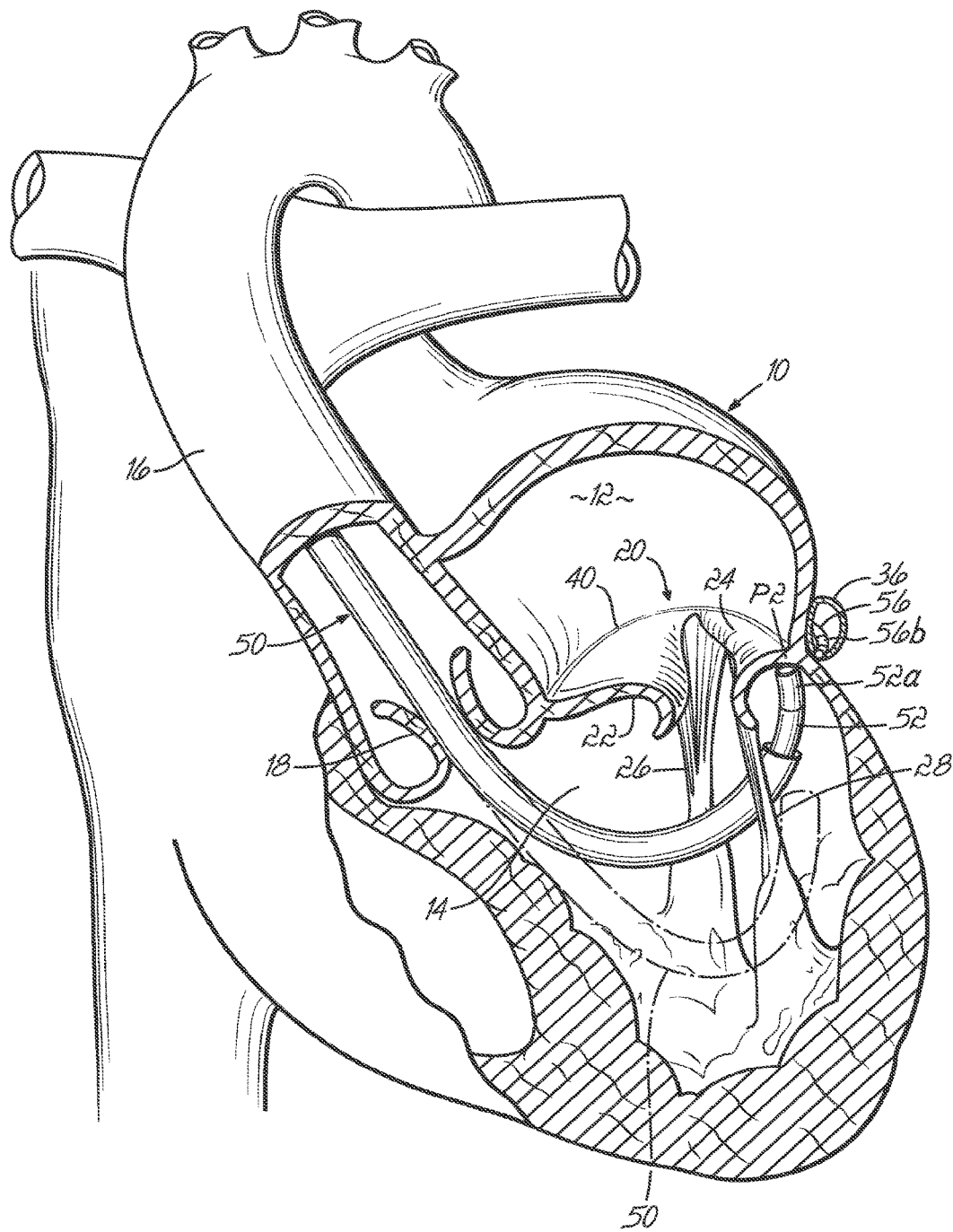
FIG. 4 is a partial longitudinal cross sectional view of the heart showing the positioning of the catheters in the left ventricle and coronary sinus.

Referring first to FIGS. 1-4, a guide catheter 50 is illustrated as being directed into the vascular system of a patient, such as through an artery in the groin region of the patient, as shown in FIG. 1. The guide catheter 50 may be a 12 mm catheter directed through the vascular system in any suitable manner. As shown, guide catheter 50 is directed into the aorta 16, through the aortic valve 18 and into the left ventricle 14 between the pair of cordae tendonae 26, 28 as best shown in FIG. 4. This guide catheter 50 is then used as a guide sheath or tube for guiding all of the subsequent catheter devices into the left ventricle 14 for use in a method of plicating the annulus 40 of the mitral valve 20. It will be appreciated that other methods of guidance may be used as alternatives or in a supplemental fashion to the various methods disclosed herein. After initial insertion of the guide catheter 50, a P2 catheter 52 is inserted to the guide catheter 50. As known in the art, "P2" refers to the central location of the base of the posterior leaflet 24 along the annulus 40. The P2 catheter 52 may have a deflectable tip to allow more accurate and easier manipulation and location of the catheter tip relative to the annulus 40. The catheter tip can include a radiopaque marker 52a visible under a fluoroscope. A coronary sinus or CS catheter 56 is directed into the coronary sinus 36 via the vascular system of the patient, such as through an entry point in the jugular vein of the patient and subsequently through the right atrium 38 as shown best in FIGS. 2 and 3. The CS catheter 56 is directed into the coronary sinus 36 as shown in FIG. 3 such that three radiopaque markers 56a, 56b, 56c on or in the catheter 56 are located generally at positions approximating P1, P2 and P3 along the mitral valve annulus 40. In this regard, the coronary sinus 36 runs generally along the mitral valve annulus 40 in most patients and therefore provides a good location for placement of markers 56a, 56b, 56c. The distal tip 52a of the P2 catheter 52 is aligned at the annulus 40 as shown in FIG. 4 such that it is directed upward at the interior of the left atrium 12. Radiopaque marker 56b in the coronary sinus 36 is used to determine and ensure proper placement of the distal tip at the P2 location along the annulus 40. Contrast media injections into the LV and/or LA may also be made to confirm positioning under a fluoroscope, for example.

Figure 5:
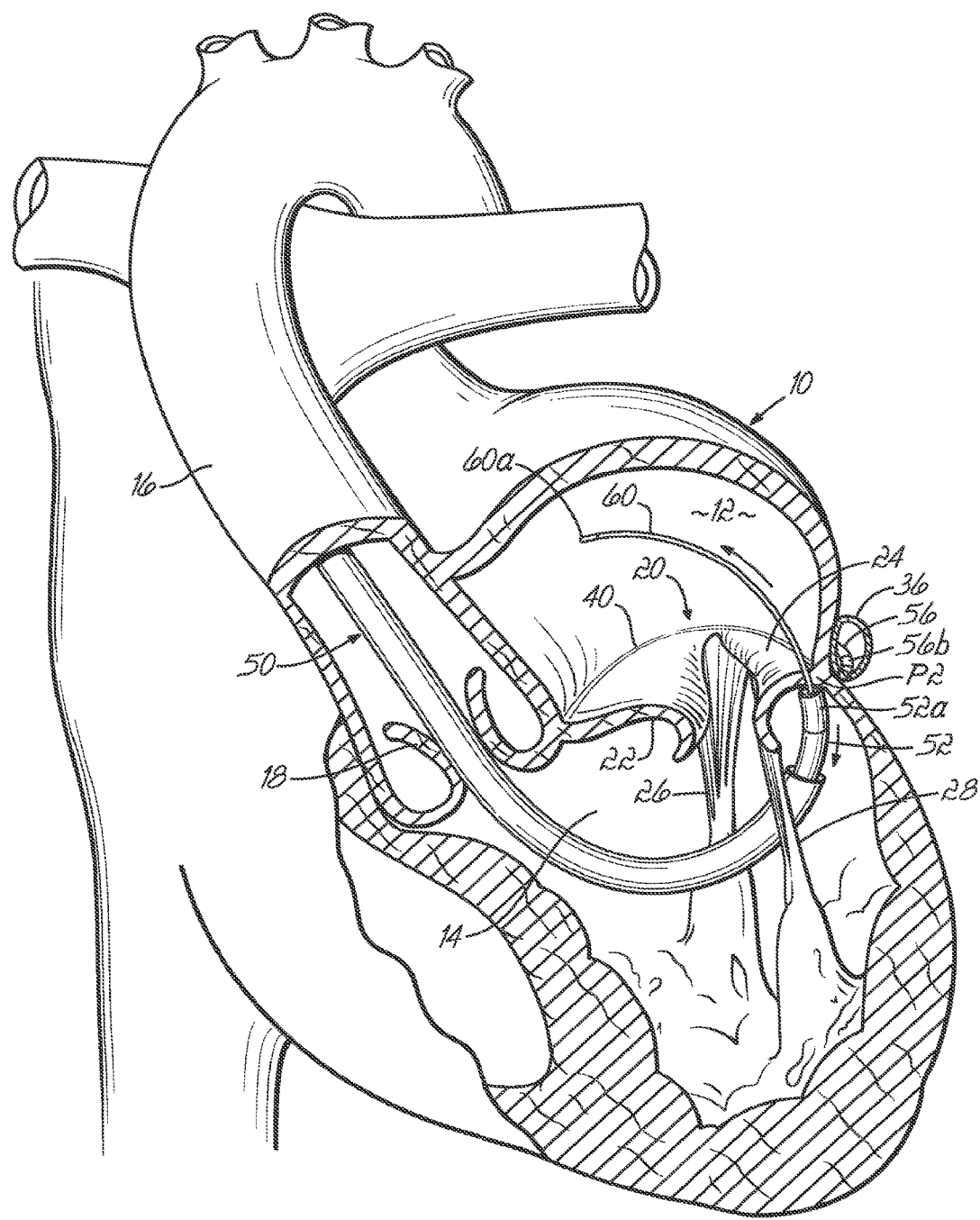
FIG. 5 is a cross sectional view of the heart similar to FIG. 4, but illustrating the further introduction of a guide wire through the mitral valve annulus.

Referring to FIG. 5, when accurate positioning of the P2 catheter 52 has been confirmed using a fluoroscope, for example, a first RF guide wire may be introduced through the P2 catheter. The P2 guide wire may have a radio frequency (RF) energy delivery tip 60a for assisting with penetration through mitral tissue generally at the annulus 40. For this purpose, a suitable RF energy device (not shown) may be coupled to guide wire 60, as well as the other RF guide wires disclosed hereinbelow. The distal portion of the P2 guide wire 60 then extends into the left atrium and curls back on itself to help prevent tissue damage within the left atrium 12 as shown best in FIG. 6.

The method then involves the further introduction of respective P1 and P3 guide wires 62, 64 through the use of a triple lumen catheter 70 contained within a sheath 72. Triple lumen catheter 70 and sheath 72 are introduced into the guide catheter 50 after withdrawal of the P2 catheter 52 therefrom. Triple lumen catheter 70 more specifically comprises a central or first catheter member 74 having a lumen 74a threaded over the P2 guide wire 60. In addition to this first or P2 catheter member 74, triple lumen catheter 70 further comprises second and third catheter members 76, 78 respectively corresponding generally to the P1 and P3 locations generally along the posterior mitral annulus 40. The second and third catheter members 76, 78 also include respective lumens 76a, 78a containing respective guide wires 62 and 64. It will be appreciated that other locations along the annulus 40 may be chosen in addition to or instead of those discussed illustratively herein.

Figure 7:
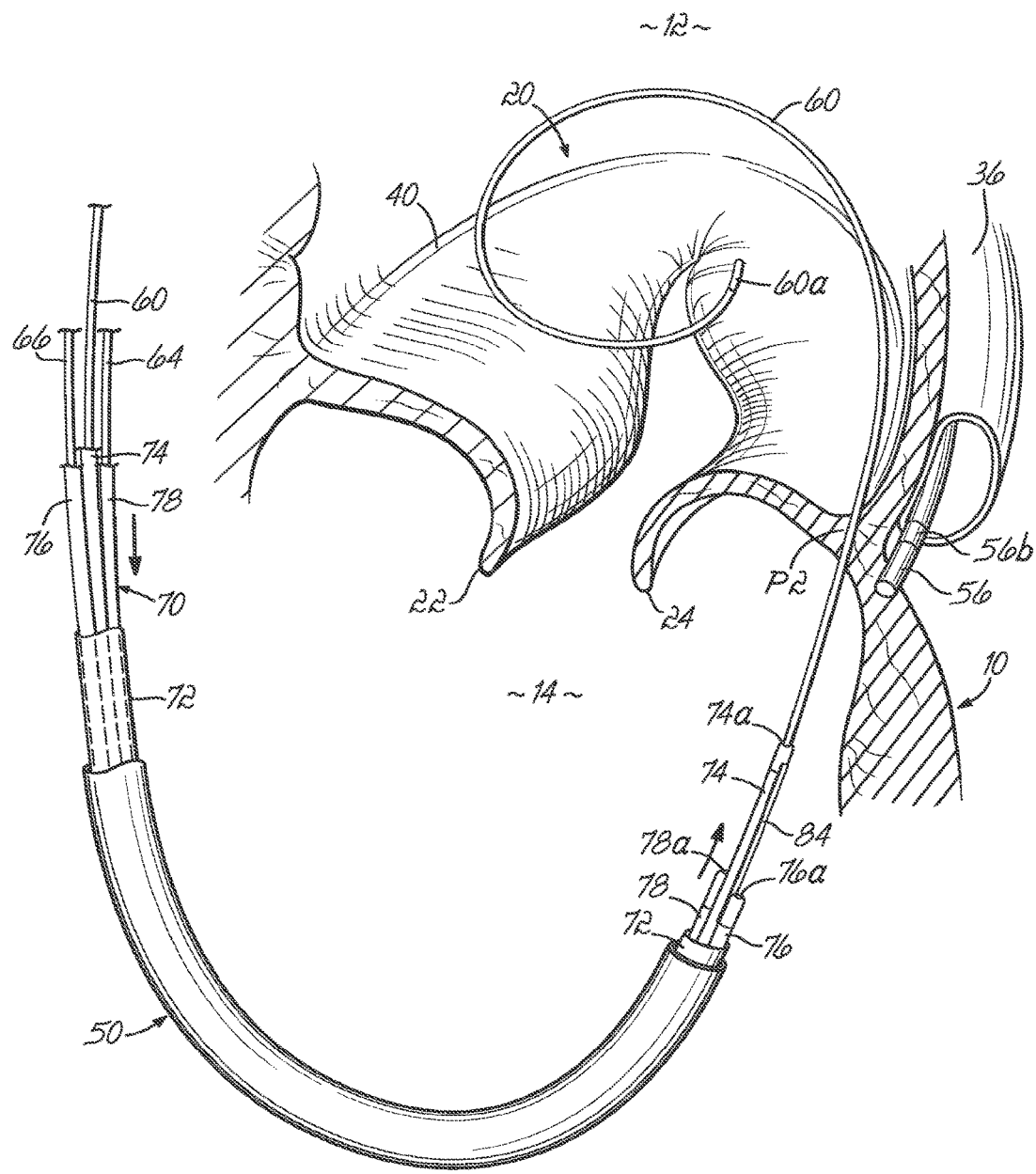
FIG. 7 is a cross sectional view of the mitral valve similar to FIG. 6 and showing the further introduction of the expandable triple lumen catheter.
Figure 8:
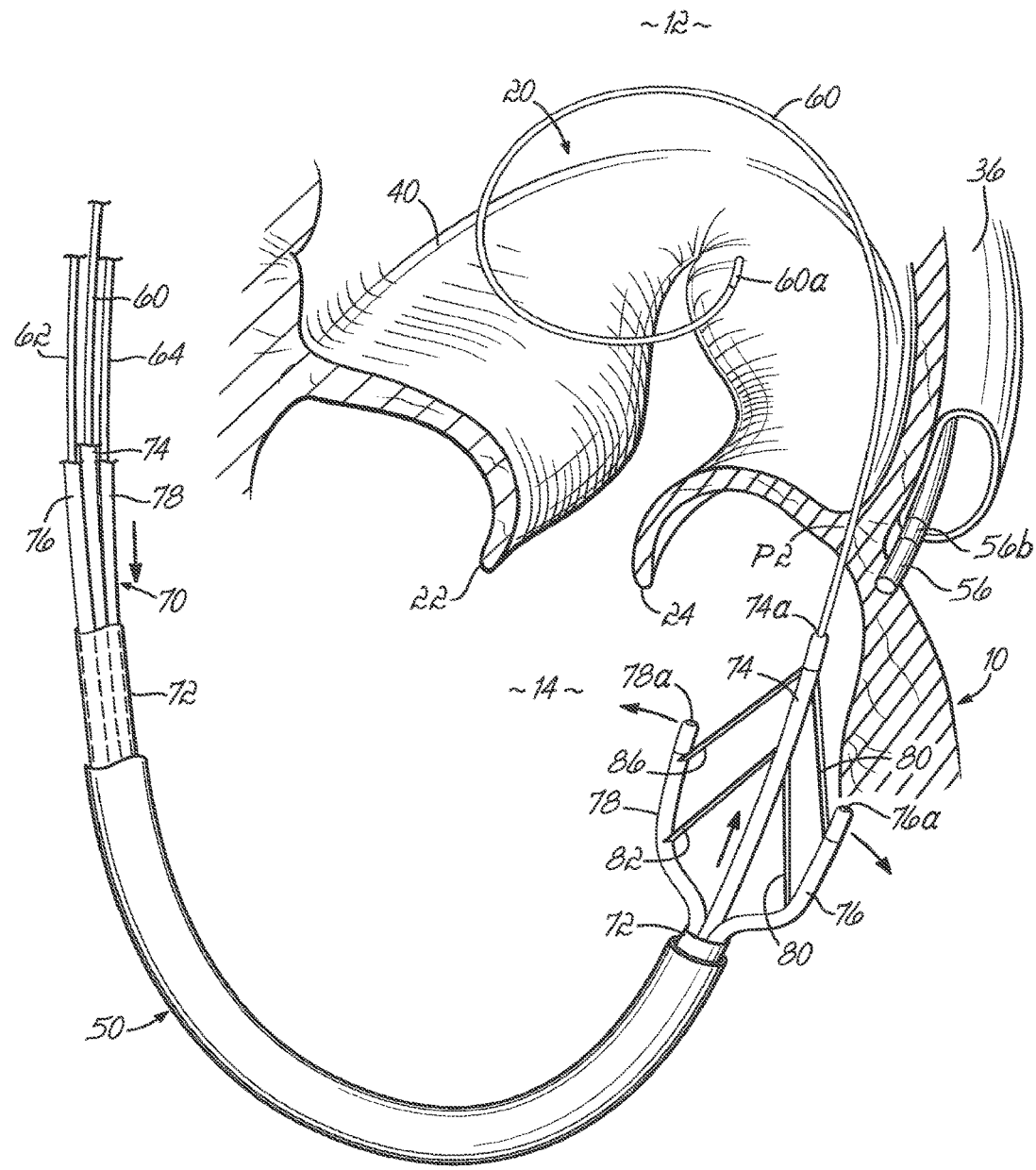
FIG. 8 is a cross sectional view of the heart similar to FIG. 7, but illustrating the initial expansion of the triple lumen catheter.
Figure 9:
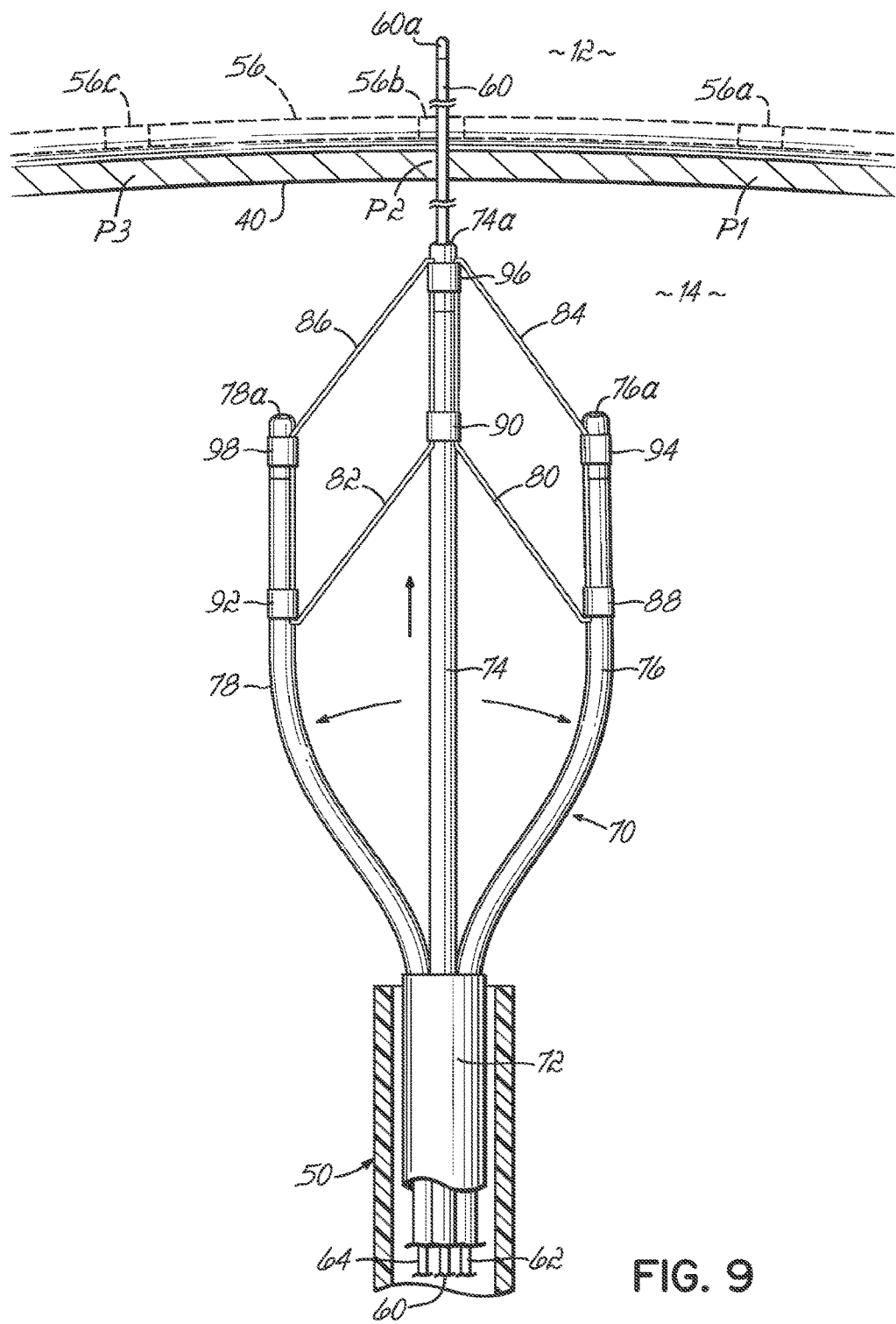
FIG. 9 is an elevational view of the expanding triple lumen catheter relative to the mitral valve annulus.

As further shown in FIG. 7, the combined triple lumen catheter 70 and sheath 72 are pushed through the guide catheter 50 and an expandable distal portion comprised of catheter members 74, 76, 78 is then extended from the sheath 72 in the left ventricle 14 of the patient. The initial positioning of the P2 guide wire 60 ensures that the middle or P2 catheter member 74 will be an accurate reference point at P2. When the sheath 72 reaches the distal location shown in FIGS. 7-9, the triple lumen catheter 70 is pushed outward from the distal end of the sheath 72 and expansion takes place as shown in FIGS. 8 and 9. As best shown in FIG. 9, the two outer catheter members 76, 78 (that is, the P1 and P3 catheter members) automatically expand outward due to their coupling with the central or P2 catheter member 74 by way of connecting bars 80, 82, 84, 86. These connecting bars may, for example, be formed from thin metallic plate material such as superelastic material, stainless steel, other metals or combinations of materials. It has been found that a thin plate of Nitinol™ (nickel-titanium) stacked adjacent to a thin plate of stainless steel works well for each connecting bar 80, 82, 84, 86. The Nitinol exhibits spring characteristics effective for the expansion of the two outer catheter members 76, 78 away from the inner or central catheter member 74, while the stainless steel plate of each connecting bar provides additional stiffness for support purposes.

Respective connectors 88, 90, 92, 94, 96, 98 couple each connecting bar 80, 82, 84, 86 to the respective catheter members 76, 74, 78 as shown in FIG. 9 with a living hinge adjacent each connector 88, 90, 92, 94, 96, 98. This illustrative structure therefore essentially forms two four-bar type linkage structures with one being formed by catheter members 74, 76 and bars 80, 84 and the other being formed by catheter members 74, 78 and bars 82, 86. This expandable structure therefore causes the two outer catheter members 76, 78 to translate distally and also expand laterally outward to known positions dictated by the respective lengths of the bars 80, 82, 84, 86. In this example, the distal end of catheter 76 is ultimately positioned approximately at position P1 along the mitral annulus 40, while the distal end of catheter member 78 is positioned approximately at position P3 along the mitral annulus 40. It will be appreciated that these positions are representative and illustrative only and that the method may be performed at any other positions along the mitral annulus 40 depending on the desires of the surgeon and needs of the patient, for example.

Figure 6:
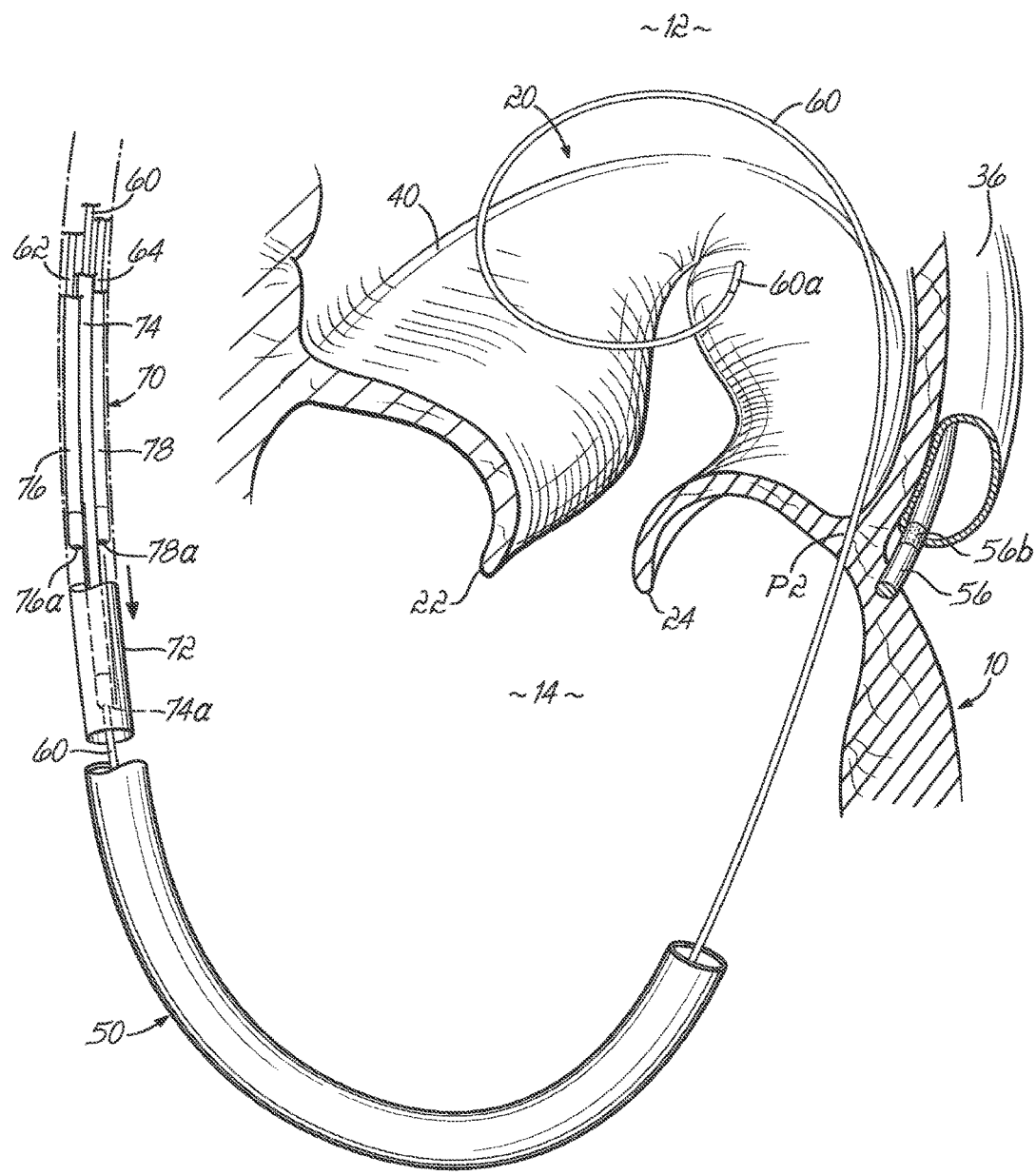
FIG. 6 is an enlarged view of the mitral valve in cross section and showing the introduction of an expandable triple lumen catheter into the left ventricle.
Figure 10:
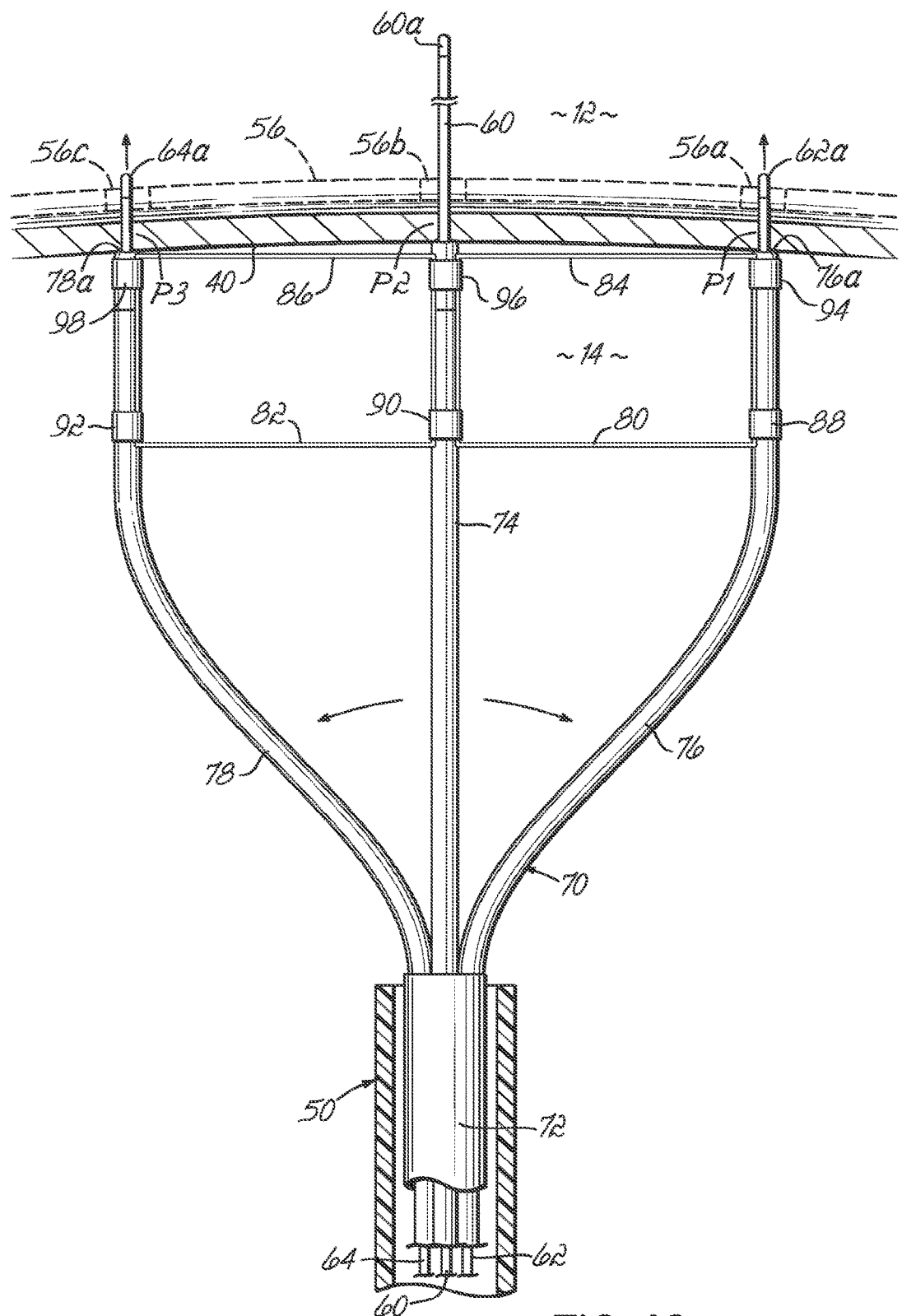
FIG. 10 is a view similar to FIG. 9, but showing the full expansion of the triple lumen catheter.

Catheter members 76, 78 include lumens 76a, 78a from which the respective P1 and P3 guide wires 62, 64 may be directed as shown in FIG. 10. Like the P2 guide wire 60, the P1 and P3 guide wires 62, 64 may include RF or radiofrequency energy delivery tips 62a, 64a for assisting with penetration through the annulus tissue 40. It will be appreciated that when the "annulus tissue" is referred to herein, this refers to tissue generally along the annulus 40 and may, in fact, be tissue on the base of the posterior leaflet 24 itself. As shown in FIG. 10, these guide wires 62a, 64a may generally align with the radiopaque markers 56a, 56c of the CS catheter 56 located in the coronary sinus 36 (FIG. 3). The RF guide wires 62, 64 are inserted through the annulus tissue 40 such that distal portions thereof extend into the left atrium 12 in manners similar to RF guide wire 60 as generally shown in FIG. 6. The triple lumen catheter 70, including the sheath 72, is then removed from the guide catheter 50.

Figure 11:
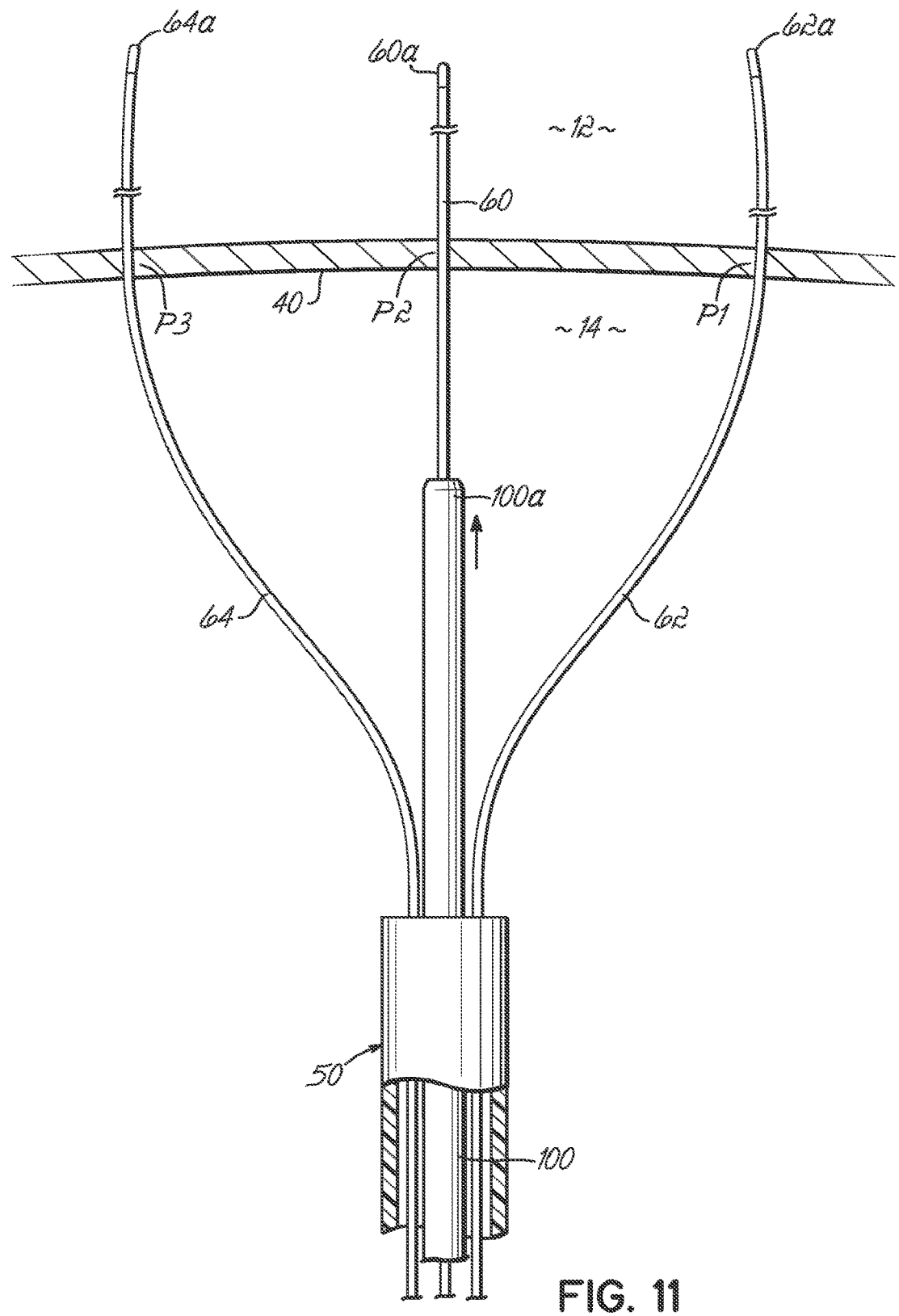
FIG. 11 is an elevational view showing the introduction of an anchor delivery catheter over one of the guide wires.
Figure 12:
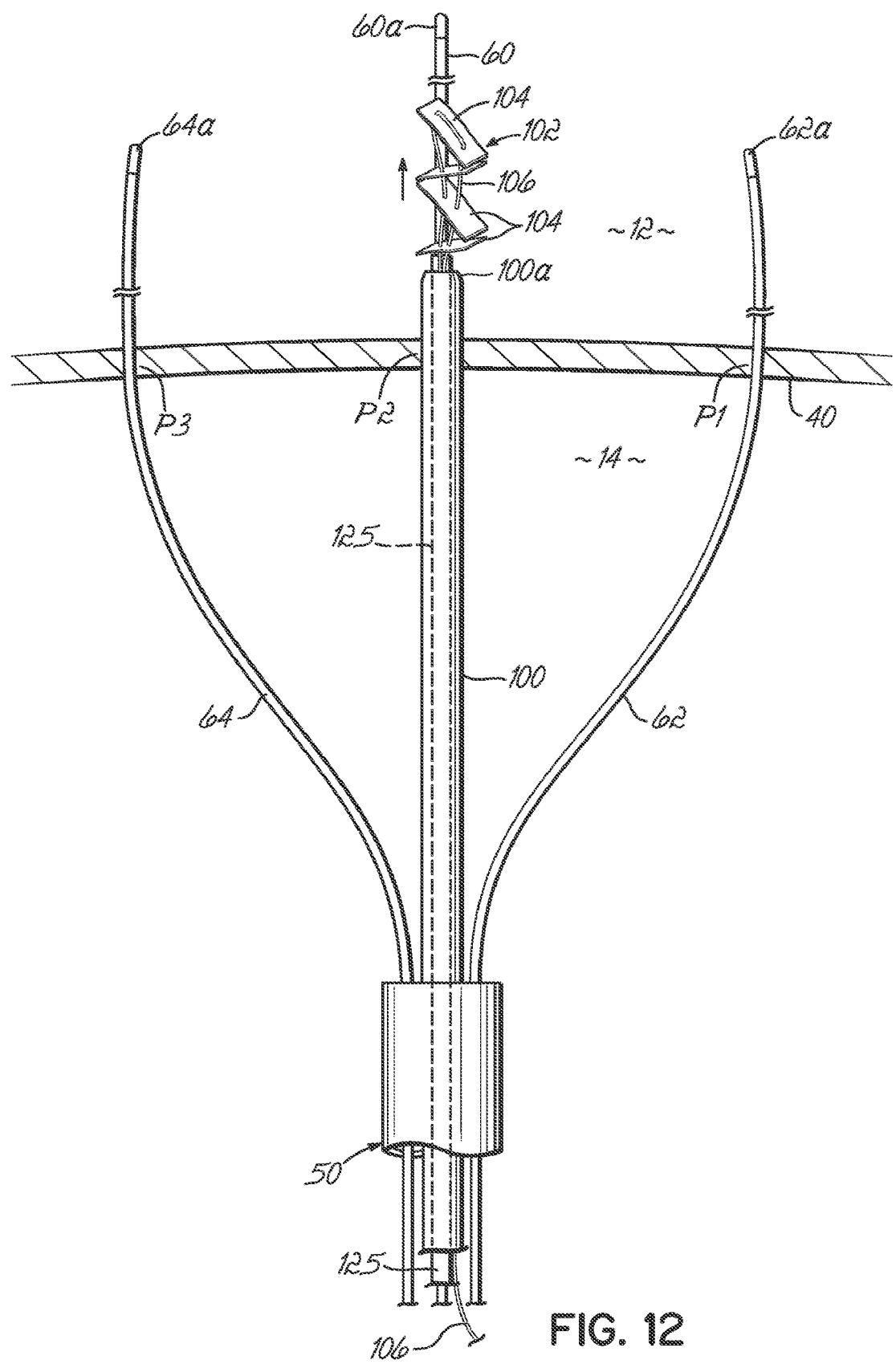
FIG. 12 is a view similar to FIG. 11, but showing the initial deployment of the anchor from the anchor delivery catheter.
Figure 12A:
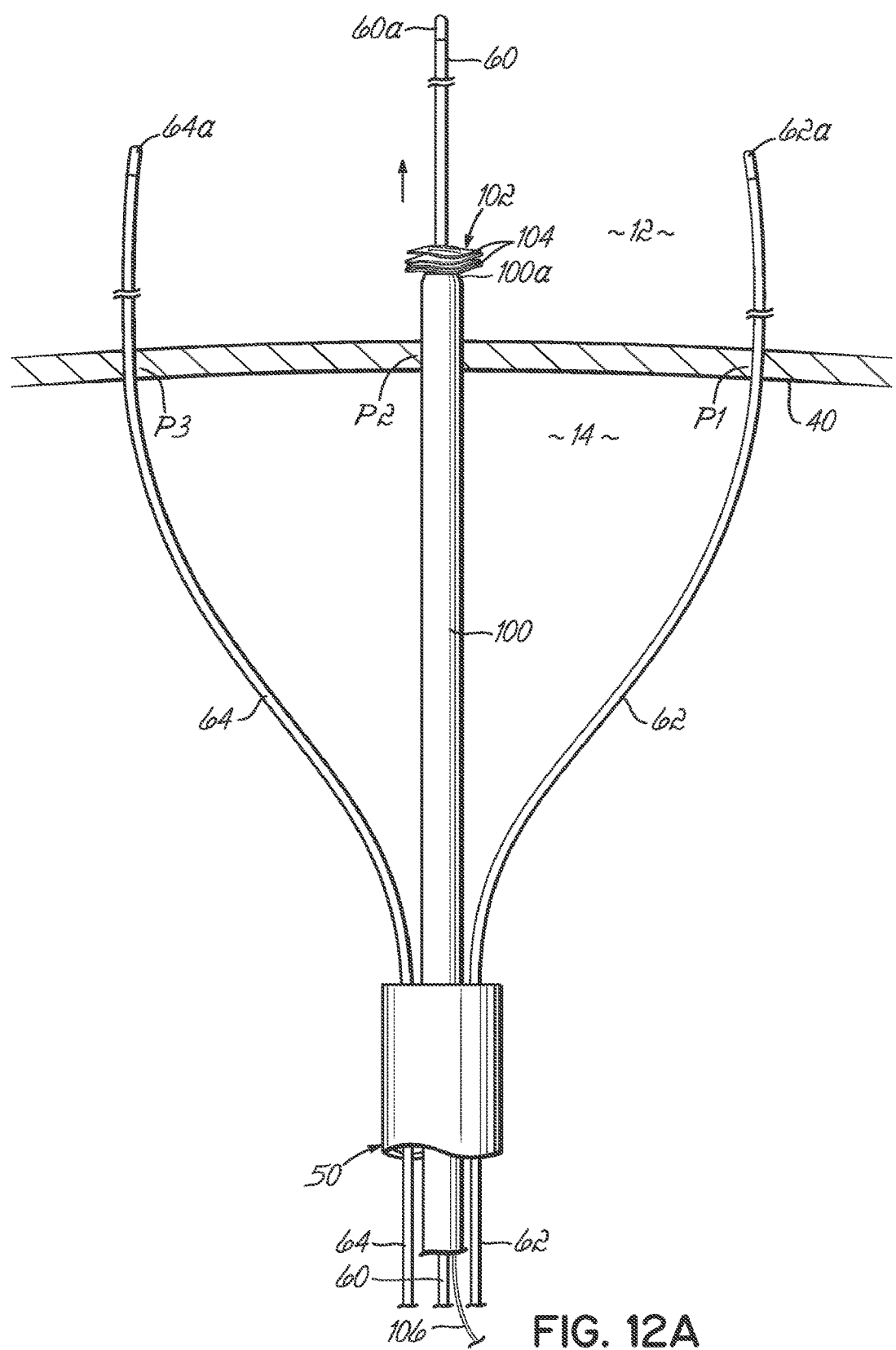
FIG. 12A is a view similar to FIG. 12, but showing a portion of the anchor compressed or shortened on a distal side of the tissue.
Figure 13:
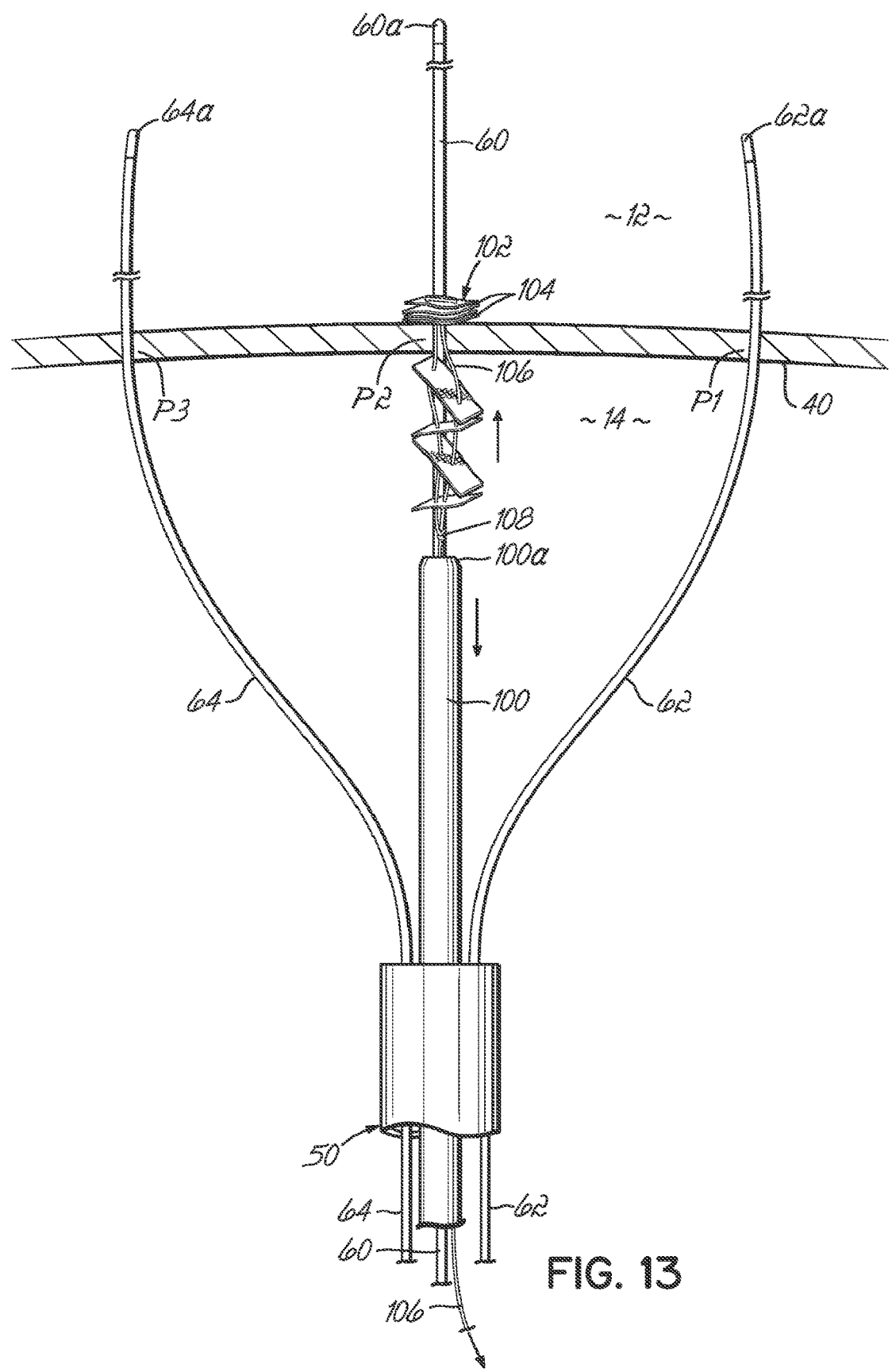
FIG. 13 is a view similar to FIG. 12, but illustrating the full deployment of the anchor from the anchor delivery catheter and the anchor delivery catheter being retracted.
Figure 14:
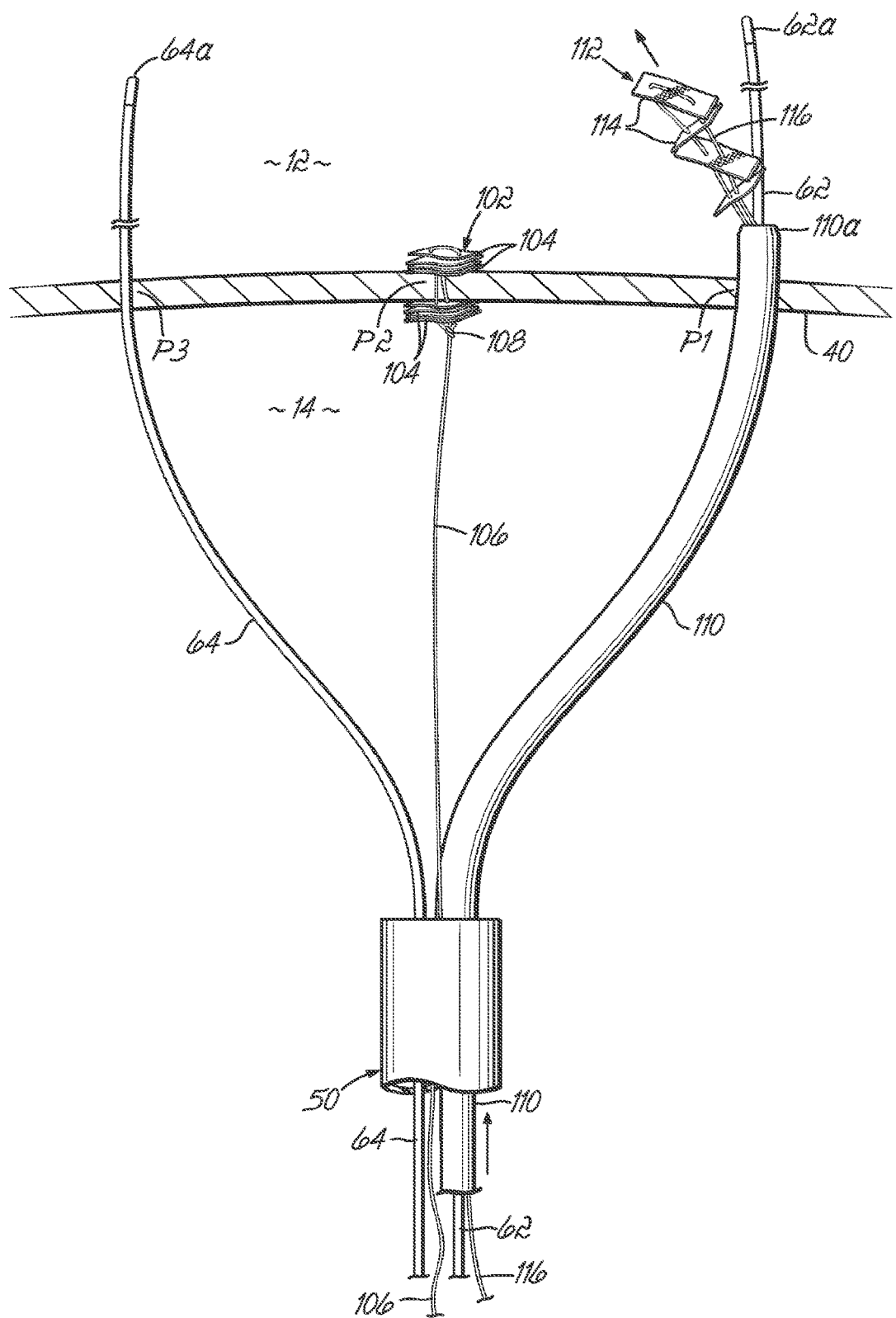
FIG. 14 is a view similar to FIG. 13, but illustrating deployment of a second anchor from an anchor delivery catheter.

FIGS. 11-15 illustrate the procedure for attaching anchors to the annulus tissue 40. In particular, FIG. 11 shows the initial introduction of a P2 anchor delivery catheter 100 over P2 guide wire 60. As further shown in FIG. 12, the distal end 100a of P2 anchor delivery catheter 100 is pushed along RF guide wire 60 until it penetrates through the annulus tissue 40. As further shown in FIG. 12, after the distal end 100a is penetrated through the annulus tissue and into the left atrium 12, an anchor assembly 102 is partially deployed as shown. In this embodiment, the anchor assembly 102 comprises a plurality of discrete, flat flexible anchor elements 104 coupled to a flexible tensile member, for example, in the form of a suture 106. It will be appreciated that in other forms or embodiments of the invention, other anchors (sometimes referred to as fasteners, plicating elements, etc.) may be used instead. As needed, the guide wire 60 may be removed before or after the anchor deployment process. As further shown in FIGS. 12A and 13, the P2 anchor delivery catheter 100 is pulled back into the left ventricle 14 and the remaining proximal portion of the anchor assembly 102 is then deployed from the distal end 100a such that a portion of the anchor elements 104 are located in the left atrium and another portion of the anchor elements are located in the left ventricle. The anchor elements 104 are coupled to the suture 106, in this example, by threading the suture 106 upwardly through the elements 104 and then back downwardly through the anchor elements 104 as shown. A slip knot 108 is then formed, or another type of lock member is used, so that when a proximal end portion of the suture 106 is pulled, all of the anchor elements 104 will be drawn together against opposite sides of the annulus tissue 40 as shown in FIG. 14. This leaves a long "tail" of the suture 106 outside the patient's body for subsequent tensioning and plication as will be described below. One or more of the anchor elements 104 may have a radiopaque marker, such as radiopaque marker 232a shown in FIG. 23, 104a for better visualization under a suitable viewing device during the procedure. For example, one such marker may be located on a proximal portion of the anchor 102 and one may be located on a distal portion of the anchor 102. Alternatively or in addition, the suture material or other flexible tension members discussed herein may have one or more radiopaque areas for better visualization.

As shown in FIG. 14, a P1 anchor delivery catheter 110 is threaded over the P1 guide wire 62 through guide catheter 50 after the P2 anchor delivery catheter 100 has been removed. An anchor assembly 112 again comprised of discrete, flat flexible anchor elements 114 is deployed through a distal end 110a of the P1 anchor delivery catheter 110 in the same manner as described above with respect to anchor assembly 102. Like anchor assembly 102, anchor assembly 112 includes a flexible tensile member, such as a suture 116, having a slip knot or other lock member for drawing the anchor elements 114 together against opposite sides of the annulus tissue 40.

Figure 15:
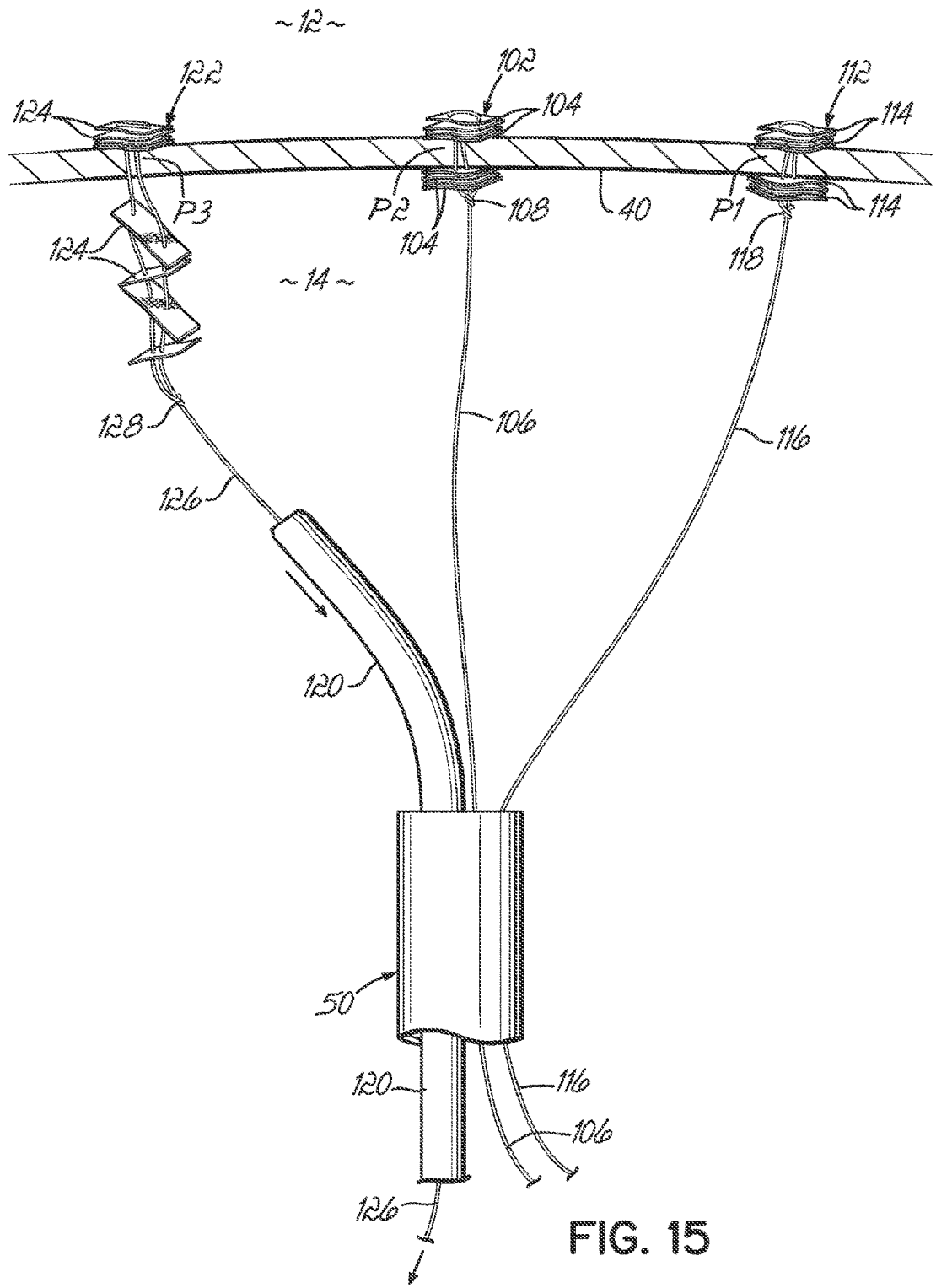
FIG. 15 is a view similar to FIG. 14, but showing the deployment of a third anchor from an anchor delivery catheter and retraction of the anchor delivery catheter.

Likewise, FIG. 15 illustrates a third or P3 anchor delivery catheter 120 used in the same manner as anchor delivery catheters 100, 110 for deploying a third or P3 anchor assembly 122 comprised of discrete, flat flexible anchor elements 124 coupled by a flexible tensile member, such as a suture 126, and capable of being drawn together against opposite sides of annulus tissue 40 through the use of a slip knot or other lock member 128. Anchor delivery catheters 100, 110, 120 may be separate catheters or may be the same catheter used to separately deliver the anchors or other fasteners or plicating elements. For ease of use, however, separate catheters that have been preloaded with separate anchors may be easiest to use in practice. Suitable pusher rods or elements 125 (FIG. 12) may be used to push the anchor assemblies 102, 112, 122 from their respective catheters 100, 110, 120. Other deployment methods may be used instead. Anchor elements 104, 114, 124 may be formed from a material such as a surgical grade fabric material (e.g., a polyester material such as Dacron™) designed to promote tissue ingrowth so that the anchors 102, 112, 122 become essentially encased in tissue over time. As mentioned herein, in various aspects of implementing systems and methods herein, any suitable anchor may be used. For example, other suitable anchors are disclosed in U.S. patent application Ser. No. 11/174,951, filed Jul. 5, 2005, assigned to the assignee of the present invention and the disclosure of which is hereby incorporated by reference herein.

Figure 16:
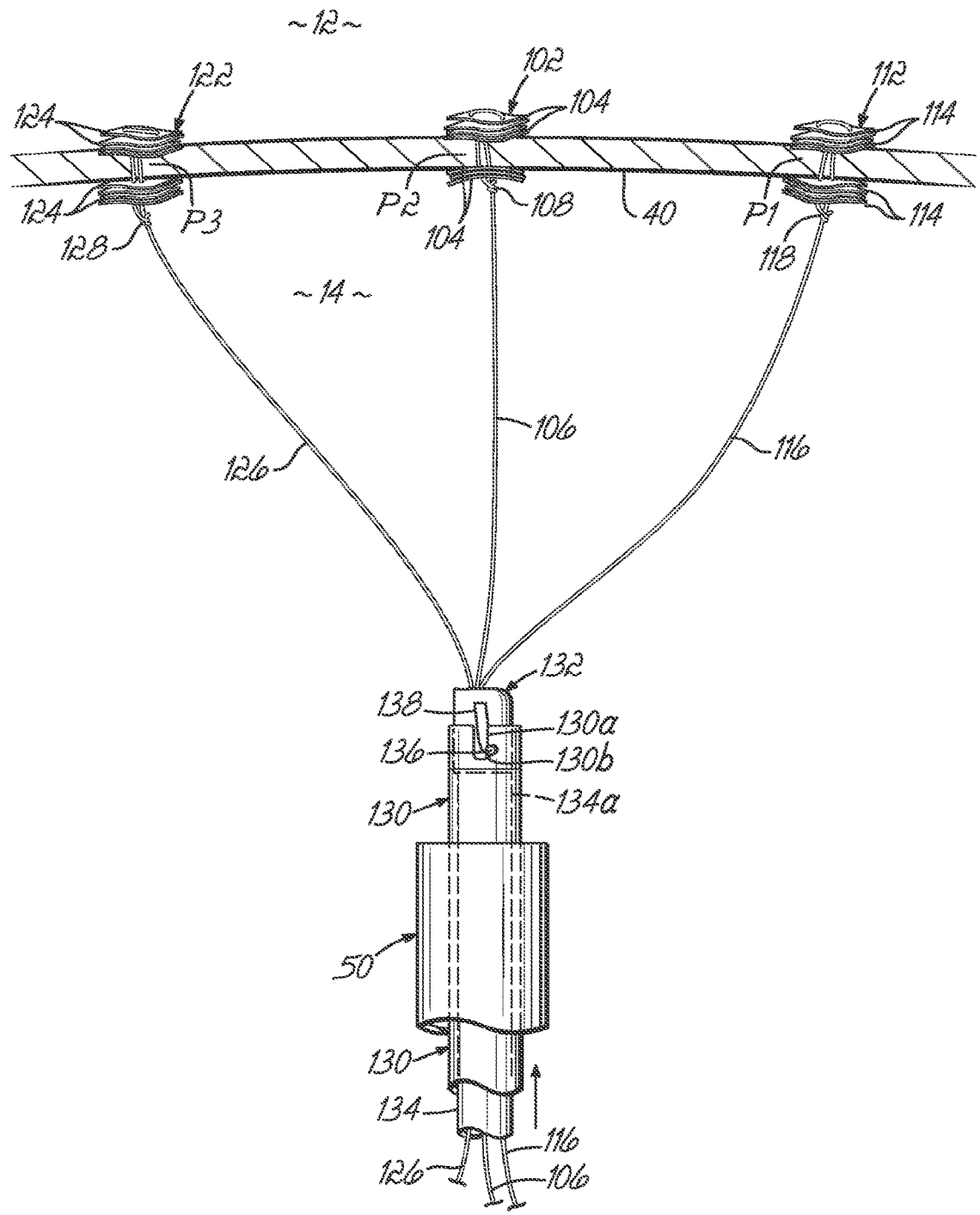
FIG. 16 is an elevational view showing the deployment of a suture locker over the three sutures associated with the respective anchors.
Figure 17:
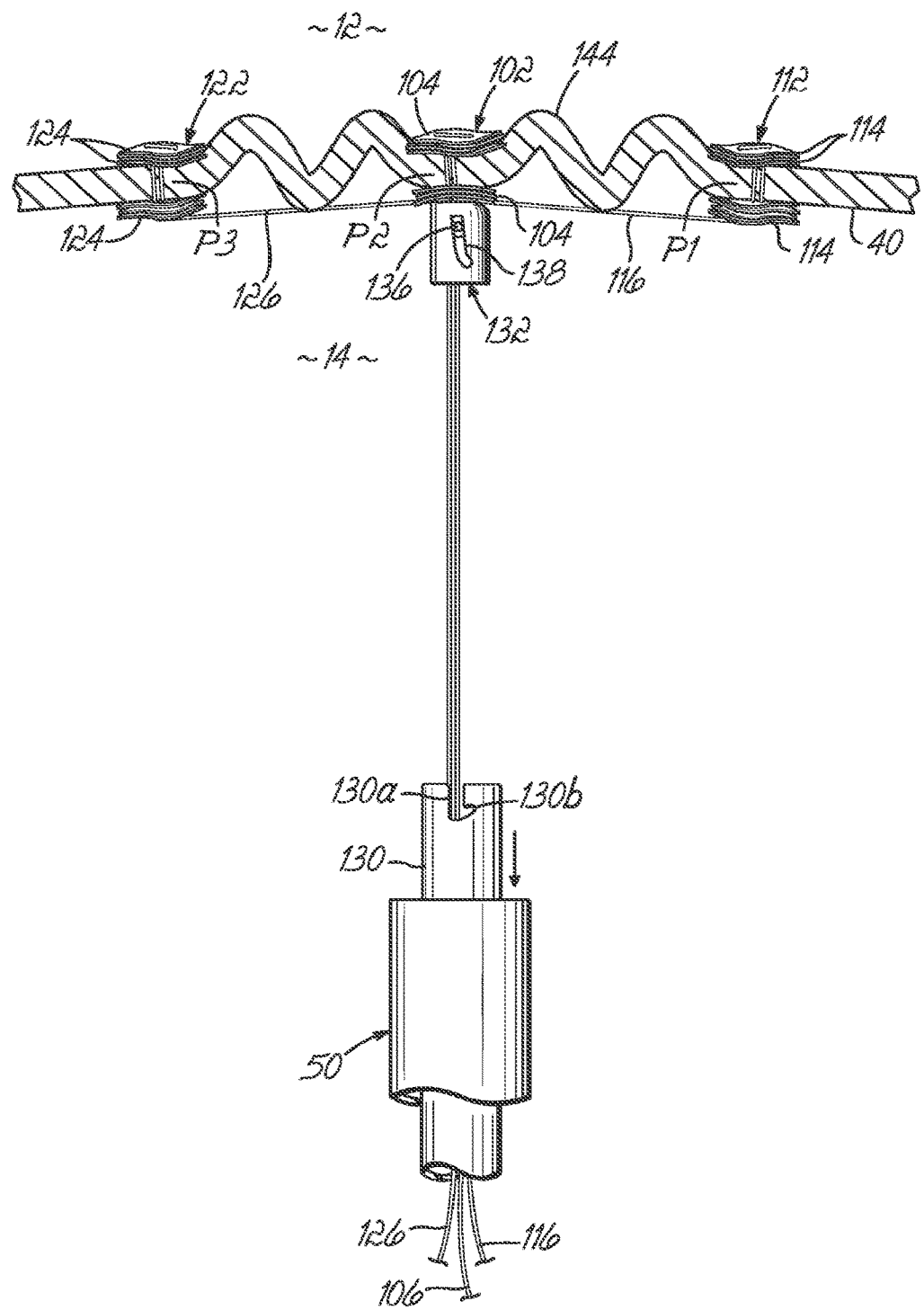
FIG. 17 is an elevational view showing retraction of the plication catheter and the mitral valve annulus in a plicated condition.

FIGS. 16 and 16A-D generally illustrate a cinching and locking procedure for plicating the mitral annulus tissue 40. Specifically, this can involve the use of an outer plication catheter 130 carrying a suture locker 132 at its distal end. An inner plication catheter 134 is received for sliding movement within the lumen of the outer plication catheter 130. The distal end 134a of the inner plication catheter 134 abuts a proximal portion of the suture locker 132. The suture locker 132 includes a slidable pin 136 having ends that are received in respective slot portions 130a, 130b of outer plication catheter 130 at its distal end. More specifically, the pin 136 is initially retained in an angled slot 130b, and in an identical slot (not shown) on the diametrically opposite side of the outer plication catheter 134, while the catheter assembly 130, 134 is directed through the guide catheter 50 into the left ventricle 14 as shown in FIG. 16. Thus, the inner catheter 134 provides an upward force against the suture locker 132 to bias the pin upwardly to the end of the angled slot 130b as shown in FIG. 16A.

After the respective sutures 106, 116, 126 have been tensioned, the cinching or plicating process and locking process may begin. In this regard, and as shown in FIG. 16B, the outer plication catheter 130 is initially moved in a distal direction as shown by the arrow in FIG. 16B, relative to the inner plication catheter 134, to force the pin 136 to ride downward in the angled slot 130b such that it is aligned with the vertical slot 130a and is pushed upwardly in the slots 138, 140 (FIG. 16C). This tightens the pin against the respective sutures 106, 116, 126 as the suture locker travels toward the annulus tissue 40. Once the desired amount of plicated tissue or folds 144 have been formed, the plication catheters 130, 134 may be withdrawn proximally through the guide catheter 50. As shown in FIG. 16C, the suture locker 132 may include a spring-like member 142 for preventing proximal movement of the pin 136 after the desired amount of plication or tightening has been achieved. For further detail on the suture locker, as well as other illustrative forms of useful suture lockers, reference is made to U.S. patent application Ser. No. 60/803,183, filed on May 25, 2006 and assigned to the assignee of the present invention, and the disclosure of which is hereby fully incorporated by reference herein. It will be understood that many types of lockers may be used for locking the anchor assemblies 102, 112, 122, or other fasteners or plicating elements in position after the desired amount of plication has been achieved. As shown, anchor elements 114, 124 may also have one or more radiopaque markers, such as radiopaque marker 232a shown in FIG. 23, as discussed above relative to anchor elements 104. Furthermore, the slip knot 108 or other lock member and/or other portions of the suture material described herein may have one or more radiopaque markers.

Figure 18:
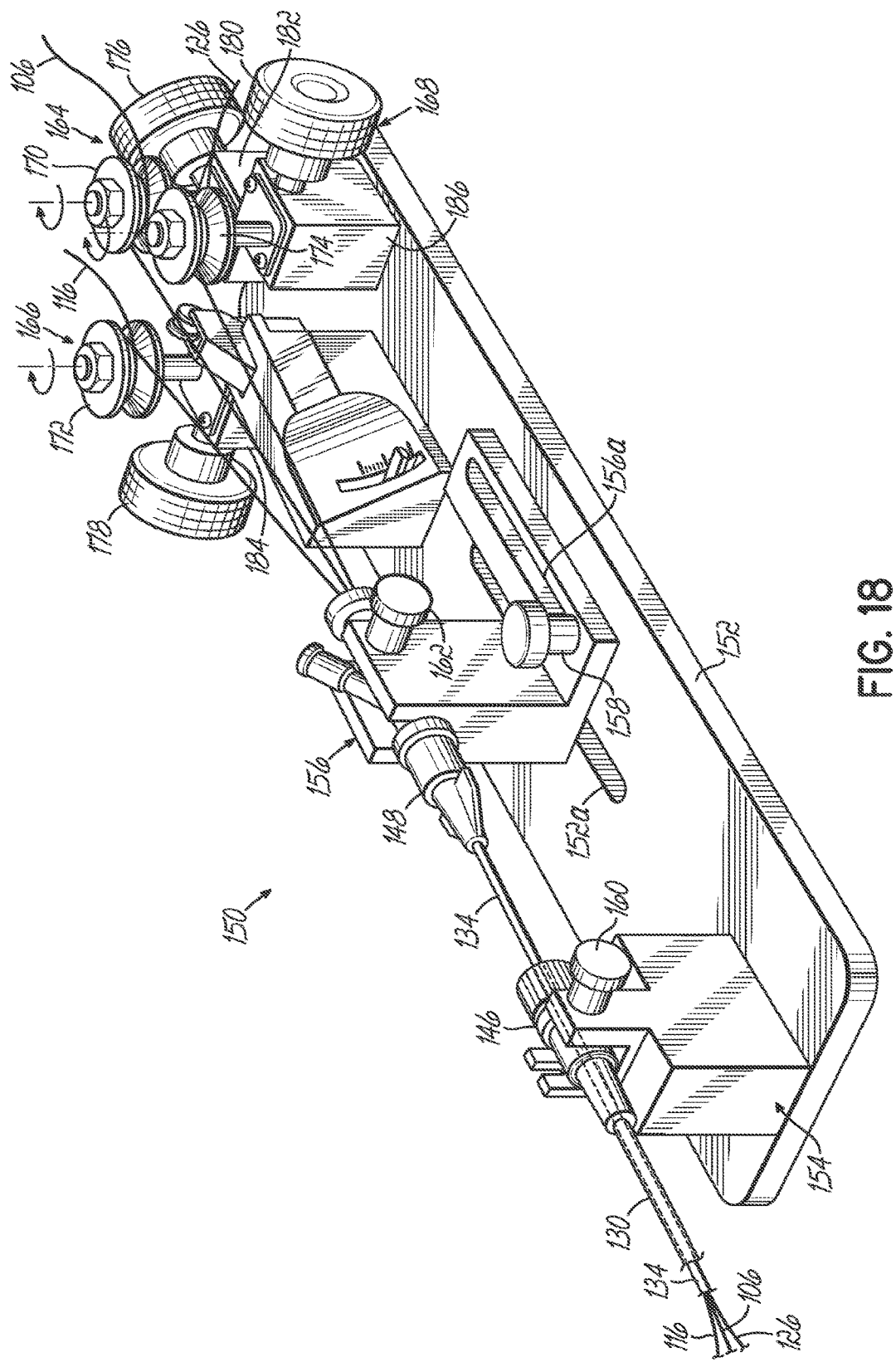
FIG. 18 is a perspective view of a plication assistance device useful for tensioning the sutures and deploying the suture locker.

As shown in FIG. 18, the outer plication catheter 130 includes a proximal hub 146 and the inner plication catheter 134 includes a hub 148. FIG. 18 illustrates a plication assistance device 150 that may be used for tensioning the respective sutures 106, 116, 126 and moving the suture locker 132 as previously described in connection with FIGS. 16, 16A-D, and 17. The plication assistance device 150 includes a support structure 152 which may take the form of a base plate 152. Base plate 152 includes a longitudinally extending slot 152a. A fixed carriage 154 is rigidly affixed to a distal end of the base plate 152 and a sliding carriage 156 is secured to a more proximal location of base plate 152. More specifically, sliding carriage 156 is affixed by a pin or other structure (not shown) so that it may slide along slot 152a. For this purpose as well, sliding carriage 156 includes a longitudinally extending slot 156a that is parallel to slot 152a. Slot 156a receives a slide lock 158 that may be rotated to respectively lock and unlock the sliding carriage 156 relative to the base plate 152. For this purpose, for example, the slide lock 158 may have a threaded member (not shown) that engages base plate 152. When the slide lock 158 is loosened, the sliding carriage 156 may slide along slot 152a as the slide lock 158 slides along slot 156a. The slide lock 158 may then be tightened at the desired position to fix the sliding carriage 156 at a desired location along the base plate 152.

The carriages 154, 156 also include respective catheter locks 160, 162 that may be rotated to tighten and loosen the connections between respective catheter hubs 146, 148 and carriages 154, 156. A proximal end portion of the base plate 152 includes suture tensioning mechanisms 164, 166, 168 for the respective sutures 106, 116, 126. More specifically, these mechanisms include spools 170, 172, 174 for receiving proximal end portions of the respective sutures 106, 116, 126 which may be wrapped and firmly engaged with the spools 170, 172, 174. The suture tensioning mechanisms 164, 166, 168 further comprise rotatable knobs 176, 178, 180 connected with respective right angle gear boxes 182, 184, 186 for converting rotation of the knobs 176, 178, 180 to rotation of the spools 170, 172, 174. That is, an output of each gear box 182, 184, 186 is coupled to a respective one of the spools 170, 172, 174. In this manner, each suture 106, 116, 126 may be separately pulled or tensioned by rotating the corresponding knob 176, 178, 180.

In use, the inner and outer plication catheters 130 and 134 are respectively secured and locked into the carriages 154 and 156, as shown in FIG. 18, after the suture locker 132 has been moved approximately to the position as shown in FIG. 16. In this position, the suture locker 132 is firmly held by the two catheters 130, 134 as previously described and after the sliding carriage 156 is locked down onto the base plate 152 by tightening slide lock 158. At this point, the sutures 106, 116, 126 are wrapped around their corresponding spools 170, 172, 174 and tensioned at a suitable minimum force. In the illustrative method, the tension at P1 and P3 (i.e., sutures 116 and 126) may be in the range of 2-4 lbs, while the tension at P2 (i.e., suture 106) may be in the range of 4-6 lbs. The tension at P1 and P3 is maintained high enough to sustain tissue plication, while the tension of P2 is slightly higher so as to lock or activate the locker 132 after plication occurs. More specifically, the higher tension on P2 suture 106 drives the pin 136 in the locker distally in the slot 138 relative to the body of the locker 132. Stated another way, the body of the locker 132 moves slightly proximally as the pin 136 remains stationary and grips the sutures 106, 116, 126.

Figure 18A:
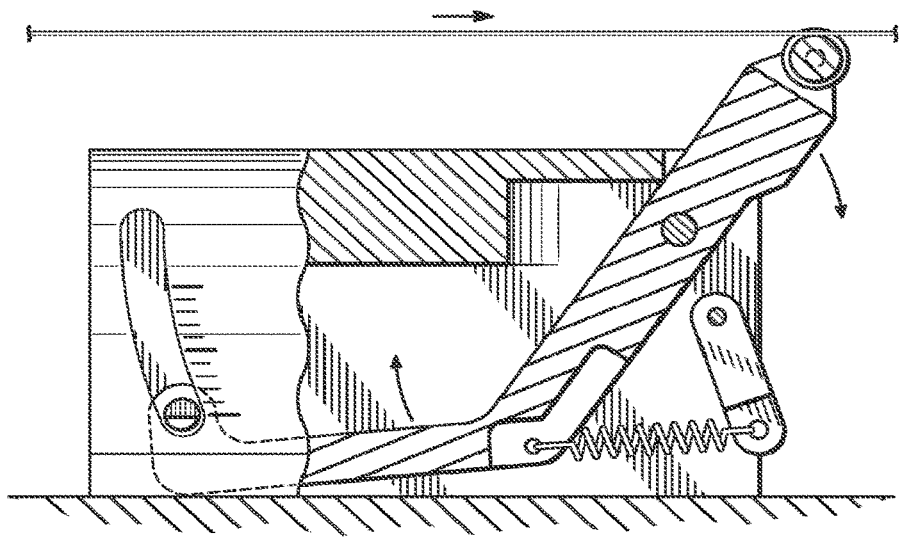
FIGS. 18A and 18B are respective partially cross sectioned views of a tension gauge associated with the plication assistance device of FIG. 18 with the sections taken lengthwise along the gauge.
Figure 18B:
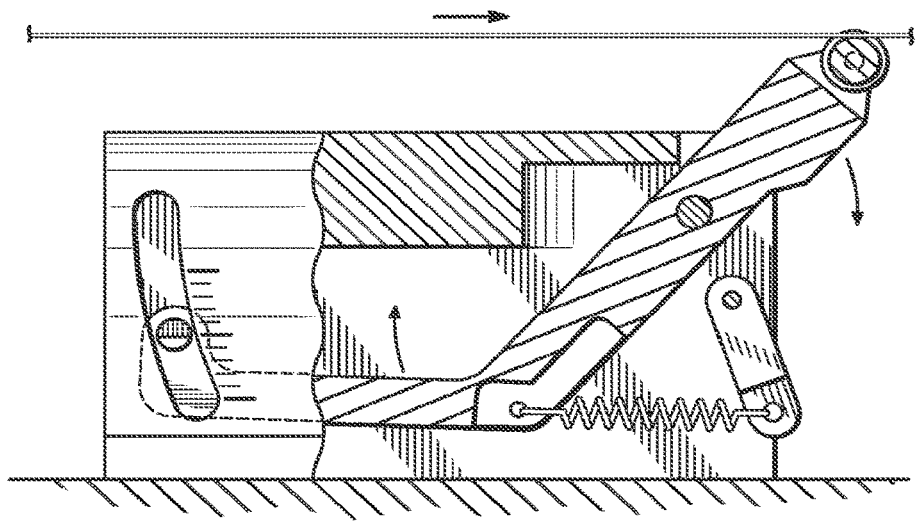

As best shown in FIGS. 18A and 18B, the plication assistance device 150 includes a tension gauge mechanism 188 for allowing the user to measure the tension of at least one of the sutures 106, 116, 126. As illustrated, the tension gauge mechanism 188 is being used to measure the tension of P2 suture 106. More specifically, this illustrative tension gauge mechanism 188 comprises a housing or other support 190 having a lever arm 192 pivotally mounted therein by way of a pivot 194. One end of the lever arm 192 includes an element such as a roller 196 for engaging the suture 106, while the opposite end includes a pin or other indicator 198 for indicating the level of tension being applied to the suture 106. A graduated scale 200 is provided in connection with the indicator 198 to indicate the tension being applied to the suture 106. Alternatively, for example, an electronic indicator and digital readout may be used. The indicator or pin 198 moves within a slot 202 in the housing 190 to allow it to be observed by the user. A spring support member 203 is also secured rigidly to the housing 190, for example, by a pin or fastener 204, or is simply a part of the housing or support 190, and does not allow pivotal movement of the spring support member 203. An opposite end of the spring support member 203 includes a connection point, which may be a hole 205, while an intermediate location on the lever arm 192 likewise includes a connection point, which may also be a hole 206. A coil spring 207 is connected between these two connection points 205, 206 and applies a force resistive to rotation of the lever arm 192 and upward movement of the indicator 198. Thus, this system, including the spring 207, is designed such that an applied tension in the direction of the arrow 208 will force the lever arm 192 to rotate clockwise around the pivot 194 (arrow 209) against the force of the spring 207 thereby indicating a measured amount of tension through upward movement of the indicator or pin 198 along the graduated scale 200. The scale 200, for example, may be graduated in any suitable manner depending on the needs of the procedure. In the present case, for purposes of measuring the tension on P2 suture 106, the scale 200 may be graduated to indicate forces between about 4 lbs and about 6 lbs with the middle of the range being suitable for tensioning the P2 suture 106.

This suture tension provides potential energy that moves the catheters 130, 134 relative to each other and locks the suture locker 132 as previously described, after the sliding carriage 156 is unlocked by loosening slide lock 158. The plication catheters 130, 132 are then removed from the guide catheter 50 leaving the long proximal tails of the suture 106, 116, 126 extending out of the patient through the guide catheter 50.

Figure 19:
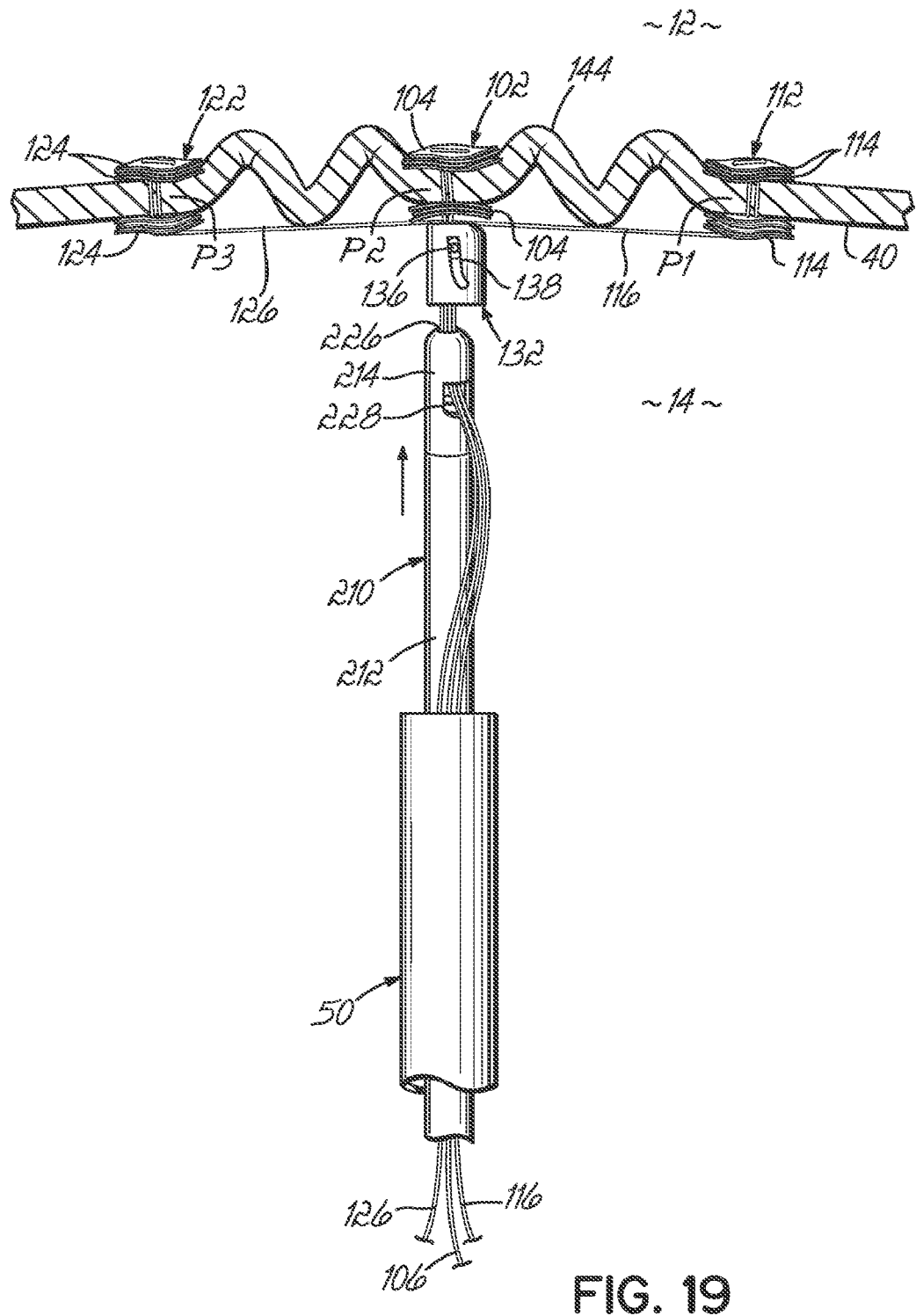
FIG. 19 is an elevational view showing the introduction of a suture cutter catheter for cutting the suture material extending from the suture locker.
Figure 20A:
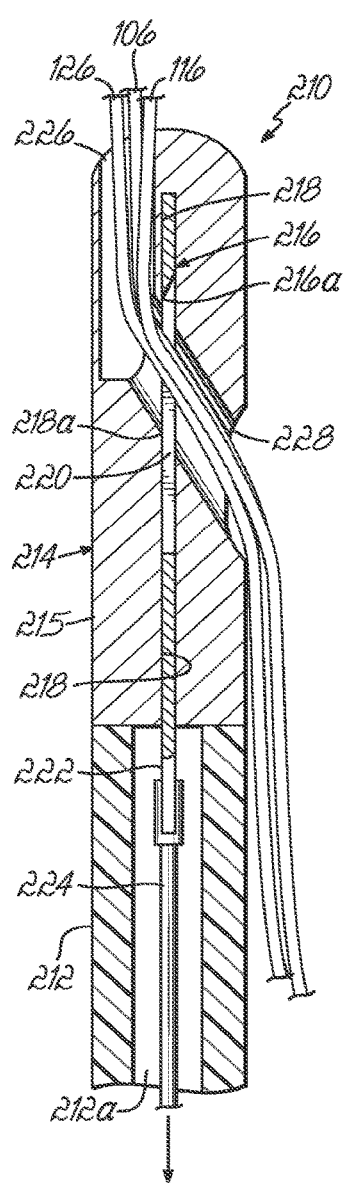
FIGS. 20A, 20B and 20C are cross sectional views of the distal end portion of the suture cutter showing the suture cutting operation.
Figure 20B:
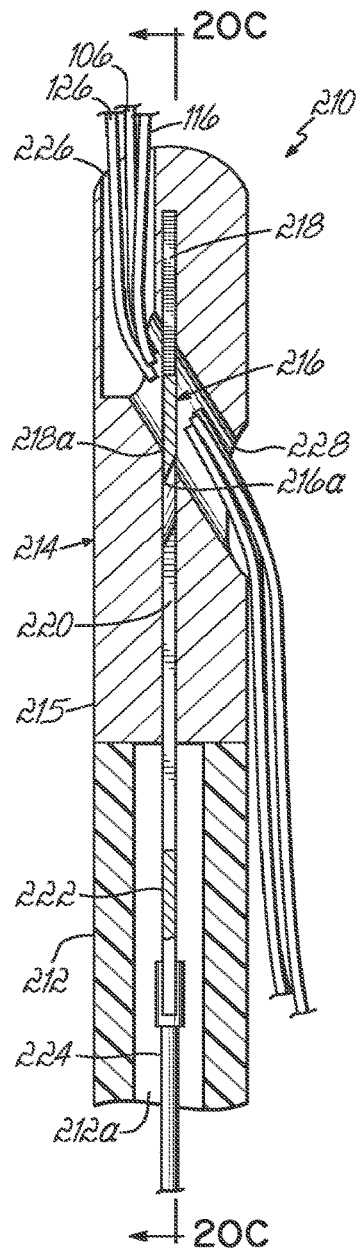
Figure 20C:
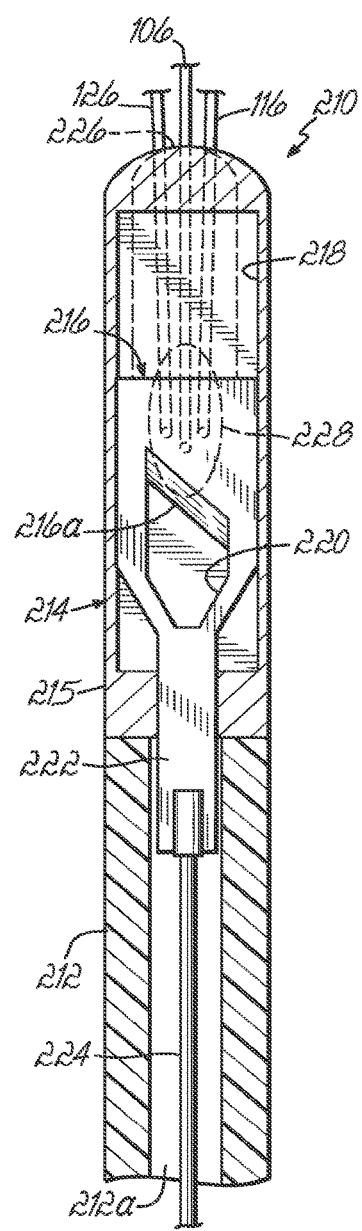
Figure 21:
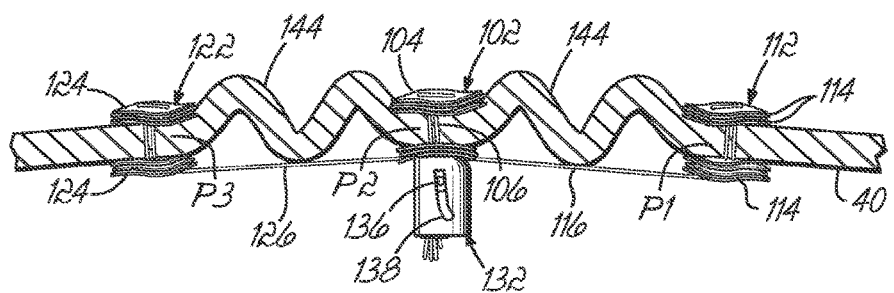
FIG. 21 is a cross sectional view of the locked anchor assembly on the plicated annulus.

A suture cutter 210 is threaded along the sutures 106, 116, 126 through the guide catheter 50 to the position generally shown in FIG. 19. In this regard, the suture cutter comprises an intermediate catheter portion 212 and a distal end portion comprising a cutting assembly 214. The cutting assembly 214 generally comprises a blade housing 215 and a reciprocating guillotine-style blade 216 slidable mounted therein. The blade 216 includes a cutting edge 216*a* as shown best in FIGS. 20A, 20B and 20C. The blade 216 is mounted for sliding, reciprocating movement within a slot 218 of blade housing 215. The blade 216 includes an opening 220 through which the sutures 106, 116, 126 extend to cross the path of the blade 216 within the housing 215. The blade further includes a connecting end 222 coupled to an actuating element 224 which may, for example, comprise a wire or other member in a lumen 212*a* of catheter portion 212. The actuating element 224 may be pulled in the direction of the arrow in FIG. 20A to move the blade 216 in a proximal direction. The user may accomplish this with a suitable handle or trigger assembly (not shown) coupled to actuator element 224 and located outside the patient. The blade housing 215 includes a first aperture 226 at its distal end and a second aperture 228 along a lateral side thereof opposite to the distal aperture 226. In this manner, the sutures 106, 116, 126 may extend into the blade housing 215 through aperture 226, opening 220 of blade 216 and then through aperture 228 as shown in FIG. 20A. As further shown in FIGS. 20B and 20C, actuating element 224 may be pulled to move the blade 216 in a proximal direction such that the cutting edge 216*a* crosses edge 218*a* with or without a shearing action to cut the sutures 106, 116, 126 at points just proximal to suture locker 132 as generally shown in FIG. 21. The cutting edge 216*a* may have a double bevel configuration instead of the single bevel design shown.

Figure 22:
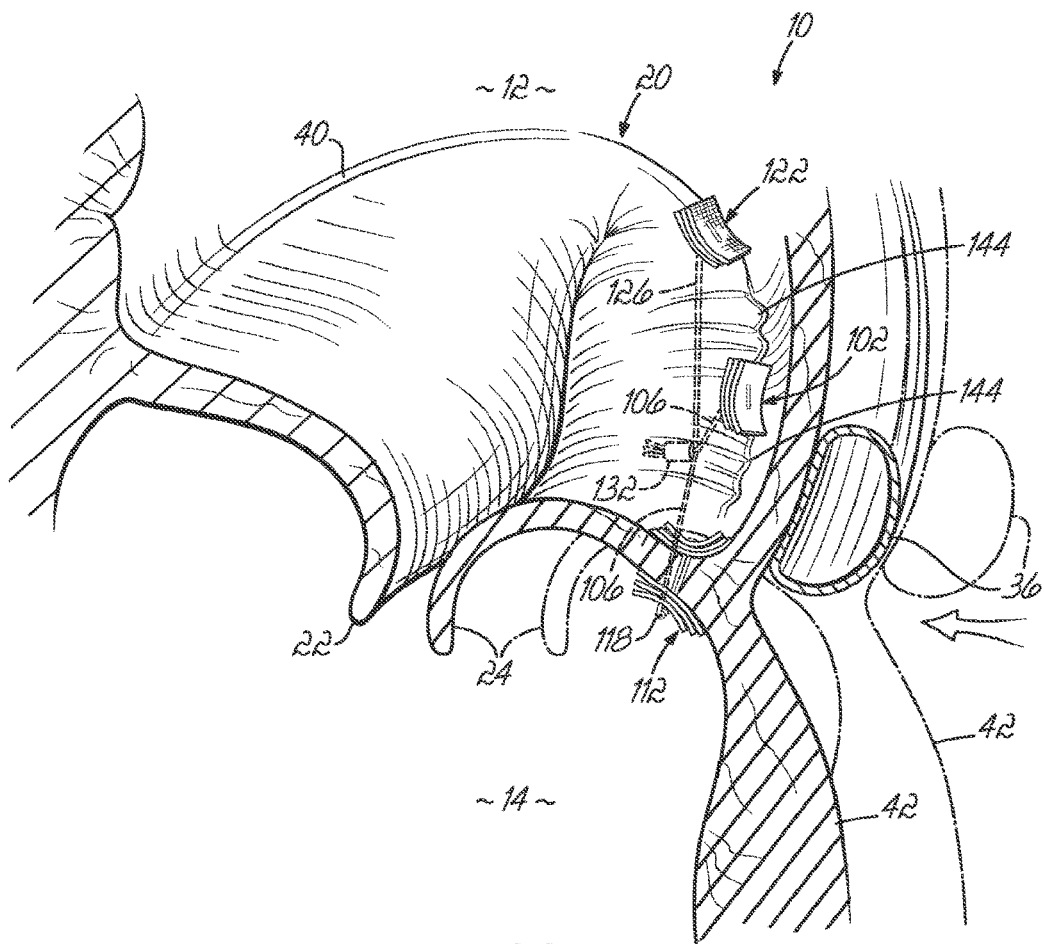
FIG. 22 is a cross sectioned view of the mitral valve showing the locked anchor assembly.

The completed annuloplasty or plication procedure is shown in FIG. 22 with the posterior leaflet 24 having been moved in an anterior direction to provide better coaptation with the anterior leaflet 22 and generally moving the posterior wall 42 of the left ventricle 14 in the same anterior direction.

Figure 23:
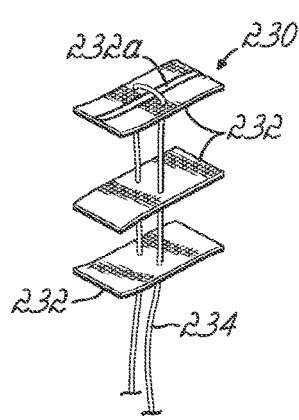
FIG. 23 is a perspective view of a first alternative anchor.
Figure 24:
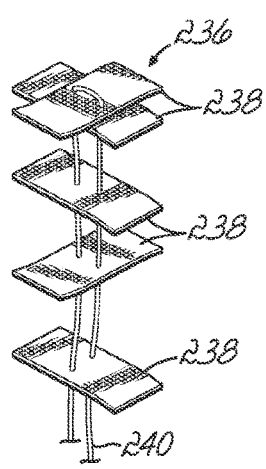
FIG. 24 is a perspective view of a second alternative anchor.
Figure 25:
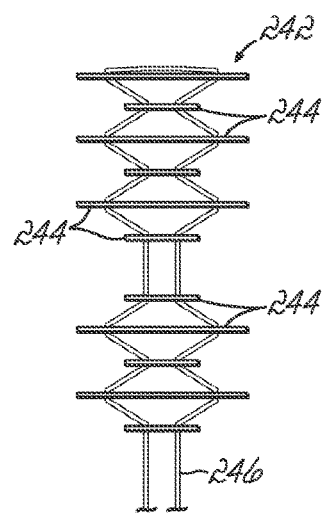
FIG. 25 is an elevational view of a third alternative anchor.

FIGS. 23-25 illustrate three additional embodiments of anchor assemblies which are only representative of the many variations and substitutions that may be made with respect to the anchor assemblies described herein. For example, FIG. 23 illustrates an anchor assembly 230 having a plurality of discrete, flat flexible anchor elements 232 coupled along a flexible tensile member such as suture 234. Unlike anchor assemblies 102, 112, 122, these anchor elements 232 are coupled to the suture 234 such that the suture extends through points separated widthwise along the rectangular anchor elements 232 as opposed to lengthwise. As previously discussed, one or more radiopaque markers 232*a* may be used. FIG. 24 illustrates an alternative anchor assembly 236 having similar discrete, flat flexible anchor elements 238 coupled along a flexible tensile member 240 with some anchor elements 238 coupled in a lengthwise fashion and some coupled in a widthwise fashion to the suture 240, as shown. FIG. 25 illustrates another alternative anchor assembly 242 comprised of discrete, flat flexible anchor elements 244 coupled for sliding movement along a flexible tensile member such as a suture 246. In this embodiment, the option of having differently sized anchor elements is shown as well as the option of having different spacing between coupling points on each anchor element 244 to create different effects, such as fabric bunching, etc. It will be appreciated that many other forms of anchor assemblies utilizing various shapes, sizes and forms of discrete elements coupled for sliding movement along a flexible tensile member may be used with various advantages.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features discussed herein may be used alone or in any combination depending on the needs and preferences of the user. This has been a description of illustrative aspects and embodiments the present invention, along with the preferred methods of practicing the present invention as currently known. However, the invention itself should only be defined by the appended claims.

What is claimed is:

1. A system for delivering respective anchors into spaced apart locations along an annulus of a mitral valve comprising:

a first catheter member having a first lumen formed therein for receiving a first guide wire so as to permit the first catheter member to move along the first guide wire; and a second catheter member that is configured to move between an expanded position and a collapsed position relative to the first catheter member, the second catheter member having a second lumen formed therein for receiving a second guide wire when the second catheter member is in the expanded position, wherein the second catheter member is fixedly connected to the first catheter member by a first connector which is configured to deploy under a select condition to automatically cause the second catheter member to move to the expanded position, the first connector defining a first living hinge adjacent to a location at which the first connector is attached about an exterior of the first catheter member and a second living hinge adjacent to a location at which the first connector is attached about an exterior of the second catheter member;

wherein the first connector comprises a first connecting bar that is configured to provide a biasing force to the second catheter member when the select condition occurs, thereby causing the second catheter member to move to the expanded position, the first connector further including: (a) a first coupling member that is coupled about the exterior of the first catheter member with a first portion of the first connecting bar being captured between the exterior of the first catheter member and the first coupling member and (b) a second coupling member that is coupled about the exterior of the second catheter member with a second portion of the first connecting bar being captured between the exterior of the second catheter member and the second coupling member.

2. The system of claim 1, wherein the first and second catheter members comprise elongated structures with the first and second lumens, respectively, being formed centrally therein.

3. The system of claim 1, further including a third catheter member that moves between an expanded position and a collapsed position relative to the first catheter member, the third catheter member having a third lumen formed therein for receiving a third guide wire when the third catheter member is in the expanded position, wherein the third catheter member is fixedly connected to the first catheter member by a second connector which is configured to deploy under a select condition to automatically cause the third catheter member to move to the expanded position.

4. The system of claim 3, wherein the second catheter member is disposed along a first side of the first catheter member and the third catheter member is disposed along a second side of the first catheter member which is opposite the first side.

5. The system of claim 3, wherein the second connector comprises a second connecting bar that is configured to provide a biasing force to the third catheter member when the select condition occurs, thereby causing the third catheter member to move to the expanded position.

6. The system of claim 5, wherein the second connecting bar comprises a third plate stacked against a fourth plate, the third plate having an elastic property to provide the biasing force and the fourth plate is configured to provide support.

7. The system of claim 6, wherein the third plate is formed of a material that provides a spring force and the fourth plate comprises a metal plate.

8. The system of claim 5, wherein the second connecting bar is configured to cause the third catheter member to translate distally and also expand laterally outward to the expanded position.

9. The system of claim 1, wherein the first connecting bar is configured to cause the second catheter member to translate distally and also expand laterally outward to the expanded position.

10. The system of claim 1, further including an outer sheath that has an inner lumen for receiving and containing at least first portions of the first and second catheter members, wherein the first and second catheter members are slidably movable within the inner lumen of the outer sheath to permit distal end portions of the first and second catheter members to be advanced distally beyond an open distal end of the outer sheath.

11. The system of claim 10, wherein the second catheter is configured to be disposed distally beyond the opening end of the outer sheath under the select condition to allow the second catheter member to automatically move to the expanded position.

12. The system of claim 1, wherein the first connecting bar comprises a nickel-titanium alloy.

13. The system of claim 1, wherein further including a second connector that is attached at one end to the first catheter member and at another end to the second catheter member, the first and second connectors being spaced from one another.

14. The system of claim 1, further including a second connector comprising a second connecting bar extending between the first and second catheter and being configured to provide a biasing force to the second catheter member when the select condition occurs, thereby causing the second catheter member to move to the expanded position, the second connector further including: (a) a third coupling member that is coupled about the exterior of the first catheter member with a first portion of the second connecting bar being captured between the exterior of the first catheter member and the third coupling member and (b) a fourth coupling member that is coupled about the exterior of the second catheter member with a second portion of the second connecting bar being captured between the exterior of the second catheter member and the fourth coupling member; wherein the first and second connecting bars are spaced apart from one another with the second connector bar being closer to distal ends of the first and second catheter members.

15. A system for delivering respective anchors into spaced apart locations along an annulus of a mitral valve comprising:
a first catheter member having a first lumen formed therein for receiving a first guide wire so as to permit the first catheter member to move along the first guide wire; and
a second catheter member that is configured to move between an expanded position and a collapsed position relative to the first catheter member, the second catheter member having a second lumen formed therein for receiving a second guide wire when the second catheter member is in the expanded position, wherein the second catheter member is fixedly connected to the first catheter member by a first connector which is configured to deploy under a select condition to automatically cause the second catheter member to move to the expanded position;
wherein the first connector comprises a first connecting bar that is configured to provide a biasing force to the second catheter member when the select condition occurs, thereby causing the second catheter member to move to the expanded position;
wherein the first connecting bar comprises a first plate stacked against a second plate, the first plate having an elastic property to provide the biasing force and the second plate is configured to provide support.

16. The system of claim 15, wherein the first plate is formed of a material that provides a spring force and the second plate comprises a metal plate.

17. A system for delivering respective anchors into spaced apart locations along an annulus of a mitral valve comprising:
a first catheter member having a first lumen formed therein for receiving a first guide wire so as to permit the first catheter member to move along the first guide wire; and
a second catheter member that is configured to move between an expanded position and a collapsed position relative to the first catheter member, the second catheter member having a second lumen formed therein for receiving a second guide wire when the second catheter member is in the expanded position, wherein the second catheter member is fixedly connected to the first catheter member by a first connecting bar which is configured to deploy under a select condition to automatically cause the second catheter member to move to the expanded position;

a third catheter member that moves between an expanded position and a collapsed position relative to the first catheter member, the third catheter member having a third lumen formed therein for receiving a third guide wire when the third catheter member is in the expanded position, wherein the third catheter member is fixedly connected to the first catheter member by a second connecting bar which is configured to deploy under a select condition to automatically cause the third catheter member to move to the expanded position; and wherein first ends of the first and second connecting bars are connected to a common first connector that is secured to the first catheter member.

18. The system of claim 17, wherein the first and second connecting bars comprise metal bars.

19. The system of claim 17, wherein the first ends of the first and second connecting bars comprise living hinges.

20. The system of claim 17, wherein further including a third connecting bar that is attached at one end to the first catheter member and at another end to the second catheter member and a fourth connecting bar that is attached at one end to the first catheter member and at another end to the third catheter member.

* * * * *